United States Patent [19]

Carlson et al.

[11] Patent Number: 5,538,852
[45] Date of Patent: Jul. 23, 1996

[54] IMMUNOASSAY FOR POLYCHLORINATED BIPHENYLS

[75] Inventors: Robert E. Carlson, Minnetonka; Todd A. Swanson, Chaska, both of Minn.

[73] Assignee: Ecochem Research, Inc., Chaska, Minn.

[21] Appl. No.: 259,046

[22] Filed: Jun. 13, 1994

Related U.S. Application Data

[63] Continuation-in-part of Ser. No. 955,846, Oct. 2, 1992, abandoned.

[51] Int. Cl.$^6$ .................. G01N 33/53; G01N 33/535; G01N 33/543
[52] U.S. Cl. ................ 435/7.9; 435/7.93; 436/518; 436/815; 436/822
[58] Field of Search .................. 435/7.9, 7.93; 436/815, 822

[56] References Cited

U.S. PATENT DOCUMENTS

| | | |
|---|---|---|
| 3,766,263 | 10/1973 | Godfrey . |
| 4,238,472 | 12/1980 | Albro et al. . |
| 4,456,691 | 6/1984 | Stark . |
| 4,468,469 | 8/1984 | Atkinson et al. . |
| 4,798,807 | 1/1989 | Vanderlaan et al. . |
| 4,865,972 | 9/1989 | Hunter . |
| 5,015,586 | 5/1991 | Severn et al. . |
| 5,145,790 | 9/1992 | Mattingly et al. . |

FOREIGN PATENT DOCUMENTS

| | | |
|---|---|---|
| 247796A1 | 12/1987 | European Pat. Off. . |
| 455058A2 | 11/1991 | European Pat. Off. . |
| 3802157A1 | 8/1989 | Germany . |

OTHER PUBLICATIONS

Van Weemen, B et al, First International Symposium on Imm. Tech. INSTRM Sym. #2, Editors Feldmann et al, 1976, pp. 125–133, Editors Feldmann et al, North Holland Publishing Company.

Erlanger, "The Preparation of Antigenic–Hapten–Carrier Conjugates: A Survey" Meth. in Enzym. vol. 70, 1980, pp. 85–95.

Voller, A et al, "Enzyme Immunoassay", in Alternative Immunoassays, editor: W. P. Collins, 1985, John Wiley & Sons Ltd., pp. 77–86.

A. L. Alford–Stevens et al., *Anal. Chem.*, 58, 2014–2022 (1986).

A. L. Alford–Stevens, *Environ. Sci. Technol.*, 20, 1194–1199 (1986).

S. Bandiera et al., *Biochemical Pharmacology*, 32, 3803–3813 (1983).

J. I. G. Cadogan, *J. Chem. Soc.*, 4257–4258 (1962).

J. I. G. Cadogan, *J. Chem. Soc.*, C1249 (1966).

M. Chamerlik–Cooper et al., "Determination of PCB's by Enzyme Immunoassay", paper presented at the Second International Symposium, Field Screening Methods for Hazardous Wastes and Toxic Chemicals, Feb. 12–14, 1991.

M. Chamerlik–Cooper et al., "Determination of PCB's by Enzyme Immunoassay", poster presented at the Second International Symposium, Field Screening Methods for Hazardous Wastes and Toxic Chemicals, Feb. 12–14, 1991.

R. E. Curry et al., *Clinical Chemistry*, 25, 1591–1595 (1979).

Dexsil Corporation brochure entitled *Clor–N–Soil* (1989).

Federal Register, 49, 43321–43336 (1984).

S. R. Finch et al., *Journal of Chromatographic Science*, 28, 351–356.

M. Franek et al., *J. Agric. Food Chem.*, 40, 1559–1565 (1992).

M. L. Gefter et al., *Somatic Cell Genetics*, 3, 231–236 (1977).

(List continued on next page.)

*Primary Examiner*—James C. Housel
*Assistant Examiner*—Ginny Portner
*Attorney, Agent, or Firm*—Merchant, Gould, Smith, Edell, Welter & Schmidt

[57] ABSTRACT

A method for determining qualitatively or quantitatively the presence of polychlorinated biphenyl in a test sample. The method includes the steps of: providing a known quantity of antibodies to polychlorinated biphenyl; providing a competitor that will bind to said antibodies in competition with polychlorinated biphenyl and having a lower affinity to said antibodies than said antibodies have to polychlorinated biphenyl; incubating said antibodies and said competitor in the presence of a test sample; and detecting the presence of polychlorinated biphenyl in the test sample. The competitor used in this method has one of the following structures:

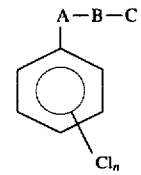

FORMULA I

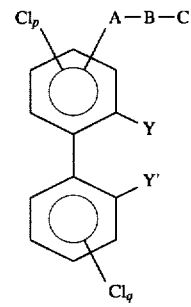

FORMULA II wherein A is selected from the group consisting of —NH—, —S—, —O—, —CH$_2$—, —NH—C(O)—, —C(O)—NH—, —NH—C(O)—NH—, —NH—C(S)—NH—, —N(CH$_3$)—, —N(CH$_3$)$_2$—, and —O—C(S)—NH—; B is preferably a single bond or an organic or inorganic group; C is selected from the group consisting of —CO$_2$H, —NH$_2$, —CHO, and —OH; Y and Y' are selected from the group consisting of —H and —Cl; n=0–5; p=0–3; and q=0–4.

22 Claims, 4 Drawing Sheets

OTHER PUBLICATIONS

J. A. Goldstein, *Chem.–Biol. Interactions*, 17, 69–87 (1977).

M. Goto et al., *Chemosphere*, No. 5, 233–238 (1974).

R. O. Harrison et al., *Program Preview*, 105th AOAC Annual International Meeting and Exposition, Phoenix, Arizona, Aug. 12–15, 1991.

R. O. Harrison et al., *Proceedings: 1991 EPRI PCB Seminar*; G. Addis, Ed.; Baltimore, MD (Oct. 8–11, 1991).

R. O. Harrison et al., "Analysis of PCB's By Enzyme Immunoassay", presented at the 8th Annual West Testing & Quality Assurance Symposium, Arlington, VA, Jul. 13–17, 1992.

K. Higuchi, *PCB Poisoning and Pollution*, Academic Press, New York (1978).

Horiba Instruments, Inc. brochure entitled "Total Sulfur & Chlorine Analyzer Model MESA–200" (1982).

K. W. Hunter, *Chem. Abs.*, 111, 110882, Abstract No. 111:110880e (1989).

S. Jensen, et al., *Nature*, 224, 247–250 (1969).

J. F. Kearney et al., *J. Immunol.*, 123, 1548–1550 (1979).

N. Koga et al., *Xenobiotica*, 19, 1307–1318 (1989).

J. Lund et al., *Chemosphere*, 16, 1677–1680 (1987).

M. I. Luster et al., *Toxicology and Applied Pharmacology*, 50, 147–155 (1979).

J. F. W. McOmie et al., *Tetrahedron*, 24, 2289–2292 (1968).

D. Monroe, *Anal. Chem.*, 56, 920A–931A (Jul. 1984).

Method 8080, *Organochlorine Pesticides and PCB's*.

National Research Counsel, "Polychlorinated Biphenyls," National Academy of Science, Washington, D.C. (1979), pp. 1–10.

W. H. Newsome et al., *Intern. J. Environ. Anal. Chem.*, 10, 295–304 (1981).

D. W. Phillipson et al., *Anal. Chem.*, 52, 2328–2332 (1980).

L. Stanker et al., *Chemosphere*, 16 1635–1639 (1987).

L. H. Stanker et al., *Toxicology*, 45, 229–243 (1987).

C. R. Sutcliffe et al., *Anal. Chem.*, 61, 2682–2686 (1969).

A. Voller, "Heterogenous Enzyme Immunoassays and their Applications", *Enzyme Immunoassay*, CRC Press, p 183 (1980).

E. K. Yau et al., *Aldrichimica Acta*, 21, 106–107 (1988).

*Affinity Techniques, Enzyme Purification: Part B*; W. B. Jakoby, ed.; Academic Press, Inc.: New York, NY, 1974; pp. 1–32.

B. Dunbar et al., "Development of Enzyme Immunoassay for the Detection of Triazine Herbicides," *J. Agric. Food Chem.*, 38, 433–437 (1990).

S. Hahnau et al., "Monoclonal Antibodies for the Enzyme Immunoassay of the Mycotoxin Cyclopiazonic Acid," *J. Agric. Food Chem.*, 41, 1076–1080 (1993).

D. R. Henderson et al., "CEDIA™, a New Homogeneous Immunoassay System," *Clin. Chem.*, 32, 1637–1641 (1986).

M. Marco et al., "Development of an Enzyme–Linked Immunosorbent ASsay for Carbaryl," *J. Agric. Food Chem.*, 41, 423–430 (1993).

M. Marco et al., "Enzyme–Linked Immunosorbent Assay for the Specific Detection of the Mercapturic Acid Metabolites of Naphthalene," *Chem. Res. Toxicol.*, 6, 284–293 (1993).

S. Ostrove, "Affinity Chromatography: General Methods" in *Guide to Protein Purification, Methods in Enzymology*; 182; M. P. Deutscher, ed.; Academic Press, Inc.: San Diego, Ca, 1990; pp. 357–369.

P. Schneider et al., "Influence of the ELISA Format and the Hapten–Enzyme Conjugate on the Sensitivity of an Immunoassay for s–Triazine Herbicides Using Monoclonal Antibodies," *J. Agric. Food Chem.*, 40, 525–530 (1992).

F. Szurdoki et al., "Synthesis of Haptens and Conjugates for an Enzyme Immunoassay for Analysis of the Herbicide Bromacil," *J. Agrric. Food Chem.*, 40, 1459–1465 (1992).

R. J. Tyhach et al., "Adaptation of Prosthetic–Group–Label Homogeneous Immunoassay to Reagent–Strip Format", *Clin. Chem.*, 27, 1499–1504 (1981).

9

11

12

13

14

15

16

17

IMMUNOASSAY FOR POLYCHLORINATED BIPHENYLS

The present invention was made with government support under Contract No. 68-03-3511 awarded by the U.S. Environmental Protection Agency. The government has certain rights in the invention.

CROSS REFERENCE TO RELATED APPLICATION

This application is a continuation-in-part of U.S. patent application Ser. No. 07/955,846, filed Oct. 2, 1992, now abandoned.

TECHNICAL FIELD

This invention relates to a method for detecting the amount of polychlorinated biphenyls in a test sample by immunoassay, and to hapten and competitor reagents for use in such an analysis.

BACKGROUND OF THE INVENTION

Polychlorinated biphenyls (PCBs) are significant environmental pollutants that generally require complex and expensive methods for their analyses. Polychlorinated biphenyls are a class of discrete chemical compounds, called congeners, having the general formula $C_{12}H_xCl_y$, where x=0-9 and y=10-x. PCBs are produced by chlorinating the biphenyl compound at one through ten of the available positions to form a mono to decachlorobiphenyl.

PCBs were commercially produced as complex mixtures for a variety of uses, including dielectric fluids in capacitors and transformers. A major producer, Monsanto Corporation, marketed PCBs under the trade name Aroclor® from 1930 to 1977. Aroclor® PCBs were marketed for use in transformers, capacitors, and many other applications. Their chemical and physical stability, and their electrical insulating properties, led to the commercial utility of the PCBs.

The chemical and physical stability of PCBs is also the primary reason PCBs pose such a significant environmental contamination problem. Because PCBs do not readily degrade in the environment after disposal or dissemination, and are lipophilic, they are persistent and tend to accumulate in living organisms, such as humans and animals. In 1966, PCBs were found in eagles, herring and other Swedish environmental samples. S. Jensen, et al., *Nature*, 224, 247–250 (1969). Since then, PCBs have been shown to be nearly ubiquitous environmental pollutants, occurring in most human and animal adipose samples, milk, sediment and numerous other matrices.

As early as 1936, occupational exposure was reported to cause toxic effects, leading to establishment of workplace threshold limit values. Animal studies with both commercial mixtures and individual congeners have shown a variety of chronic toxic effects. National Research Counsel, "Polychlorinated Biphenyls," National Academy of Science, Washington, D.C. (1979). PCB contaminated cooking oil caused a total of over 1200 "Yusho" patients in 1968 in western Japan. The clinical manifestations include various somatic complaints, low birth weights, chloracne and pigmentation. K. Higuchi, *PCB Poisoning and Pollution*, Academic Press, New York (1978). The discovery of widespread environmental occurrence, increased general environmental concern, and an apparent link to carcinogenesis culminated in the regulation of PCBs under the Toxic Substances Control Act in the United States.

Several EPA rules governing the use of PCBs are of concern to analytical chemists, as they require determination of PCBs in various matrices. Restrictions on the use of PCBs in the United States and other countries has made disposal of PCBs a major concern. Large quantities of PCB containing products, such as transformer and capacitor oils, are being removed from service and must be disposed of properly. For example, in the United States, the allowed methods of disposal are keyed both to concentration and to the matrix. If the PCB concentration in a transformer oil is 500 ppm or greater, disposal in a high efficiency incinerator is required. If the concentration is between 50 and 500 ppm other methods of disposal may be used.

While PCB regulations and disposal requirements differ from country to country, there is a common analytical interest in determining the presence and amount of PCBs in the environment, and in materials that are potential sources of PCBs to the environment. Regardless of the laws and rules, the analytical needs are similar: reliable, practical, and sensitive methods that can determine PCBs in a variety of matrices.

The present methods for detecting PCBs include mass spectrophotometry, x-ray fluorescence spectroscopy, gas chromatography, and high-performance liquid chromatography. One commonly employed analytical technique involves gas chromatography with ion-capture or mass spectrometer detection. Instrumental methods are relatively accurate, but expensive and time consuming. In addition, they require sophisticated analytical instrumentation and skilled operators.

A qualitative method for detecting PCBs in soil and oil based on dehalogenation followed by detection of the liberated chloride, is commercially available from the Dexsil Corporation. This method only measures total organic chlorine, and is prone to a wide variety of interferences.

Two papers on the development of PCB immunoassays have been published. M. I. Luster, et al., *Toxicol. Appl. Pharmacol.*, 50, 147–155 (1979); W. H. Newsome and J. B. Shields, *Intern. J. Environ. Anal. Chem.*, 10, 295–304 (1981). Both papers describe the development of a radioimmunoassay (RIA) for specific PCB congeners which gave fair to poor specificity and sensitivity for the broad range of significant PCB congeners and congener mixtures. Also, U.S. Pat. No. 4,456,691, issued to S. Stark, teaches the preparation of polyclonal antibodies to PCBs using Aroclor®1254 which has been aminated, diazotized and coupled to Bovine Serum Albumin (BSA). The antisera was evaluated by an RIA. M. Frunek, et al., *J. Agric. Food Chem.*, 40, 1559–1565 (1992) teach a radioimmunoassay method for the detection of PCBs.

In European Patent Application No. 0 455 058 A2, the Applicants describe an immunoassay method for detecting the presence or amount of polychlorinated biphenyls in a test sample. It is desirable to have an immunoassay method with greater sensitivity than disclosed by Applicants in the European application.

Accordingly, there is a need for a more sensitive immunoassay, particularly one that can offer significant advantages in cost, personnel training, and equipment requirements over present immunoassays and that provides substantially improved assay performance over known methods.

SUMMARY OF THE INVENTION

Figure 1:
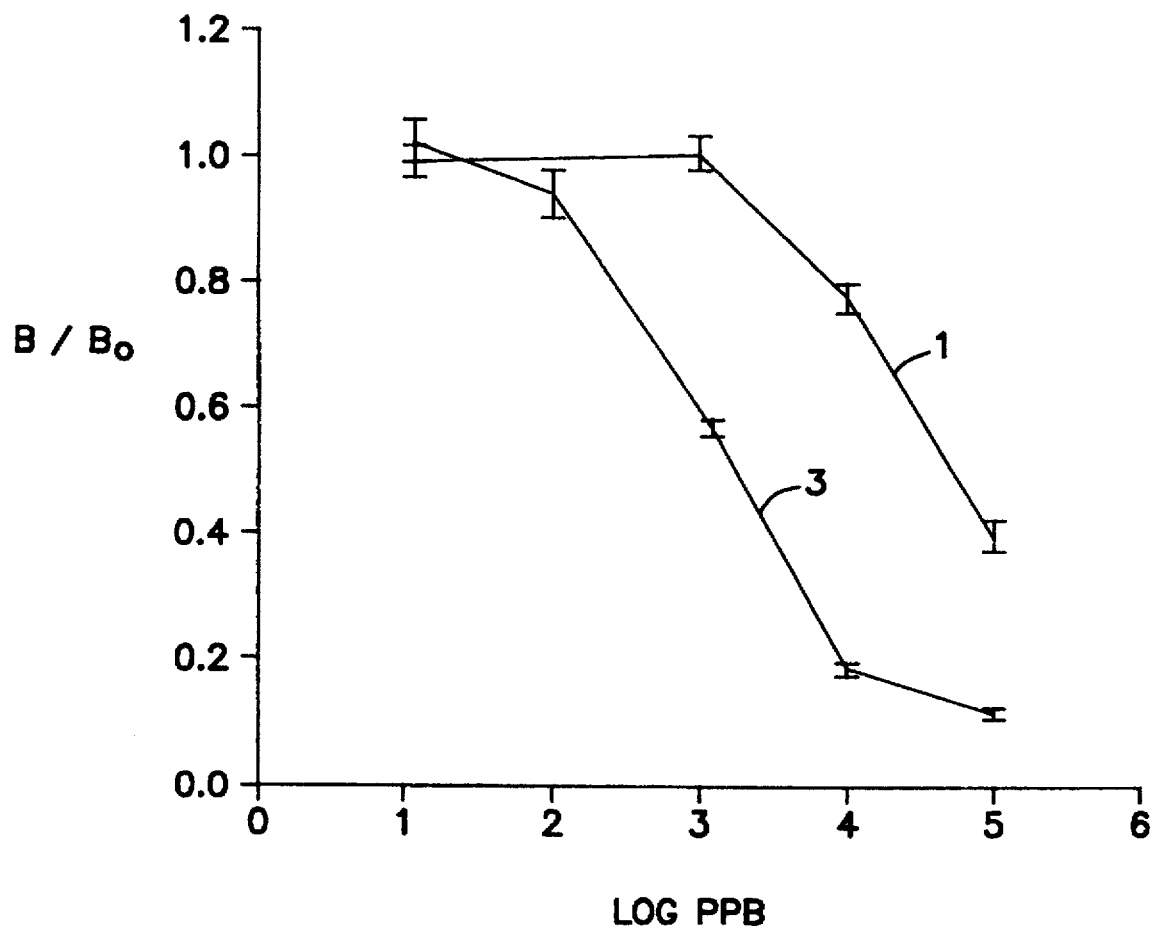
FIG. 1 is a graph of the present invention which illustrates standard curves obtained using the ELISA format, Hapten I (plot 1) or Exemplified Competitor 11 (plot 3) as the competition reagent, and Aroclor®1248 as the analyte.

The present invention provides a method of determining the presence or amount of polychlorinated biphenyl in a test sample. That is, the present invention provides both qualitative and quantitative analysis methods for PCBs. This method is an immunoassay that preferably utilizes a competitor reagent to accurately detect the presence and the amount of polychlorinated biphenyl congeners in a test sample, at greater sensitivity than currently used immunoassays. The competitors of the present invention compete with PCBs present in a test sample for binding sites on antibodies that recognize and bind to PCBs. Antibodies are raised by conjugating a hapten of the present invention with a protein carrier and injecting the conjugate into an animal. Competitors and haptens of the present invention can be used in a number of assay formats to detect PCBs at greater sensitivity.

An assay method of the present invention comprises the steps of: a) providing a known quantity of antibodies to polychlorinated biphenyl; b) providing a competitor that will bind to said antibodies in competition with polychlorinated biphenyl; c) incubating said antibodies and said competitor in the presence of a test sample; and d) detecting the presence of polychlorinated biphenyl in the test sample.

Preferably, to improve sensitivity said competitor will have a lower affinity to said antibodies than said antibodies have to the polychlorinated biphenyls. Also, the step of incubating the antibodies and competitor in the presence of a test sample is preferably carried out for a period of time sufficient to obtain a reproducible relationship between the quantity of competitor bound to the antibodies and the quantity of the polychlorinated biphenyl in the test sample. Preferably, the step of detecting the presence of polychlorinated biphenyl involves measuring the amount of polychlorinated biphenyl in the test sample, i.e., carrying out a quantitative analysis. This can occur using a labeled competitor and by measuring the amount of antibody bound to said labeled competitor. In certain embodiments, however, the detecting step involves measuring the amount of unbound competitor in the test sample.

"Test sample," as used herein, refers to a sample to be tested for the presence of PCBs. The test sample may be in liquid or solid form, and will include soil samples, oil samples, and other samples suspected of containing PCBs.

A "hapten" is a molecule that when combined with a carrier protein induces an immune response in an animal. For purposes of this invention, the hapten is designed to raise antibodies that recognize and bind to PCBs. The competitor reagents of the present invention are designed to improve the sensitivity of the assay format selected. The competitor will bind to the antibodies raised from hapten-protein complexes of the invention in competition with PCBs in a test sample.

The present invention provides novel competitors described by the following general formulas:

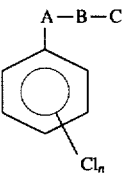

FORMULA I

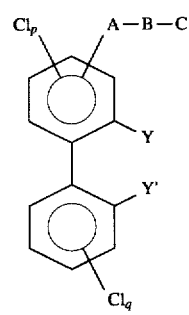

FORMULA II wherein (a) A is selected from the group consisting of —NH—, —S—, —O—, —CH$_2$—, —NH—C(O)—, —C(O)—NH—, —NH—C(O)—NH—, —NH—C(S)—NH—, —N(CH$_3$)—, —N(CH$_3$)$_2$—, and —O—C(S)—NH—, preferably —NH—, —S—, —O—, and —CH$_2$—, and more preferably —S— and —CH$_2$—;

(b) B is a single bond or an organic or inorganic group; preferably B is a single bond or a saturated or unsaturated linear, branched or cyclic hydrocarbon group; more preferably B is a single bond or a C$_1$–C$_{30}$ alkyl, most preferably a C$_1$–C$_{10}$ alkyl, optionally interrupted by 1–10 (preferably 1–4) nonperoxide —O—, —S—, or —NH— groups;

(c) C is selected from the group consisting of —CO$_2$H, —NH$_2$, —CHO, and —OH;

(d) Y and Y' are selected from the group consisting of —H and —Cl, preferably at least one of Y and Y' is —Cl, more preferably both Y and Y' are —Cl;

(e) n=0–5, preferably n=1–4, and more preferably n=1–3;

(f) p=0–3; and (g) q=0–4.

Competitors of Formula I are preferred as they are expected to provide, in general, greater sensitivity than the biphenyl based competitors of Formula II. Competitors of Formula I are expected to bind anti-hapten antibodies with a lower affinity than the affinity with which PCBs will bind to the anti-hapten antibodies. Of the competitors of Formula II, the competitors based on the alkyl link (A-B-C in Competitors 7 and 8 below) when used with antibodies raised from haptens using a polar chlorine mimic linker (e.g. —NH—, —S—, —O—, etc.) may have the best sensitivity of the competitors of Formula II. By polar chlorine mimic linker it is meant that the group which attaches the linker to the biphenyl nucleus has properties of size, electronegativity, etc. which resemble chlorine. For example, the ether (—O—) and thioether (—S—) groups are expected to be good chlorine mimic moieties while the alkyl (—CH$_2$—) group is expected to be a poorer chlorine mimic. Herein, a "linker" is represented by A-B-C in Formulas I and II and by L-M-N in Formula III.

Haptens from which antibodies for use in the present immunoassay can be raised include those described by Formula III:

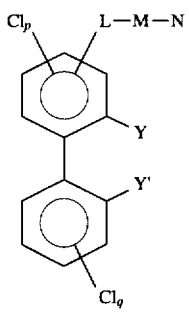

FORMULA III wherein (a) L is selected from the group consisting of —NH—, —S—, —O—, —CH$_2$—, —NH—C(O)—, —C(O)—NH—, —NH—C(O)—NH—, —NH—C(S)—NH—, —N(CH$_3$)$_2$—, —N(CH$_3$)—, and —O—C(S)—NH—, preferably —S—, —CH$_2$—, —C(O)—NH—, —NH—C(O)—NH—, —NH—C(S)—NH—, —N(CH$_3$)$_2$—, —N(CH$_3$)—, and —O—C(S)—NH—, more preferably —S—, —CH$_2$—, and —C(O)—NH—, and most preferably —S— and —CH$_2$—;

(b) M is a single bond or an organic or inorganic group; preferably M is a single bond or a saturated or unsaturated linear, branched, or cyclic hydrocarbon group; more preferably M is a single bond or a C$_1$–C$_{30}$ alkyl, most preferably a C$_1$–C$_{10}$ alkyl, optionally interrupted by 1–10 (preferably 1–4) nonperoxide —O—, —S—, or —NH—groups;

(c) N is selected from the group consisting of —CO$_2$H, —NN$_2$, —CHO, and —OH;

(d) Y and Y' are selected from the group consisting of —H and —Cl, with the proviso that at least one of Y and Y' is —Cl, preferably both Y and Y' are —Cl;

(e) p=0–3; and (f) q=0–4.

As stated above for Formulas I–III, substituent B (Formulas I and II) and M (Formula III) represent an alkyl group that is optionally interrupted by 1–10 O, S, or NH groups. That is, the alkyl group can be a straight or branched saturated carbon chain with 0–10 O, S, or NH groups within the chain. Preferably, if one or more of these groups are present they are not in sequence with each other. That is, each is bonded to two carbon atoms within the chain.

In the context of the present invention with respect to M (Formula III) and B (Formulas I and II), the term "organic group" means an aromatic, heterocyclic, saturated or unsaturated linear, branched, or cyclic hydrocarbon group. This term is used to encompass alkyl and vinyl groups, for example. The term "heterocyclic" means a mono-or polynuclear saturated or unsaturated cyclic radical containing carbons and one or more heteroatoms such as nitrogen, oxygen, phosphorus, silicon, or sulfur or a combination thereof in the ring or rings. The term "aromatic" group means a mono- or polynuclear aromatic hydrocarbon group, including arylalkyl groups. The term "arylalkyl" group means a linear, branched, or cyclic alkyl hydrocarbon radical having a mono- or polynuclear aromatic hydrocarbon or heterocyclic substituent.

DETAILED DESCRIPTION OF THE INVENTION

Background-Immunoassay

Immunoassays are based on antigen-antibody interactions. Antibodies are symmetrical serum proteins, typically with two sites that enable binding to target molecules (antigens). The antibody combining site is a complex, folded surface. Binding is influenced by hydrophobic and ionic forces as well as geometric fit. The bulk of the antibody protein is not involved in the combining site and can provide a site for covalent attachment to marker molecules, such as enzymes, radionuclides, or fluorophores.

A hapten is a small molecule (e.g., less than ca. 1000 daltons) that does not induce an immune response by itself, but is recognized by some antibodies. An immune response is induced by injecting a complex of the hapten and a protein into an animal. The complex can result from a physical association of the protein and hapten, such as is obtained from the mixing of a lipophilic hapten (e.g., PCBs) with permethylated BSA, or from a covalent interaction such that a protein-hapten conjugate is formed.

A wide range of antibodies are produced in response to immunization with a hapten-protein complex. Most of the antibodies will react with the protein alone or with some complex of the protein, hapten and linkage groups. Only a few of the antibodies produced will bind with high affinity to the hapten alone, i.e., with no contribution of the protein and/or linker to the binding site. These antibodies are the ones which are most desirable for immunoassays aimed at detecting hapten-like chemicals.

Both polyclonal and monoclonal antibodies are readily prepared and suitable for the immunoassay of the present invention. The antibodies raised from injection of a hapten-protein complex into an animal can be isolated by conventional, well-known antibody isolation techniques.

Assay

Competitors and haptens of the present invention are useful in a number of assay formats. Once suitable antibody (antisera) has been raised using a hapten of the present invention (Formula III), the antibodies and competitors of the invention (Formulas I and II) are incorporated into a suitable immunoassay. Enzyme ImmunoAssay (EIA) is a preferred format because of significant advantages in cost, personnel training and equipment requirements over radioimmunoassay and fluoroimmunoassay.

Other than enzymes, radioisotopes, luminescent molecules, fluorescent molecules, chemiluminescent molecules, and other detectable moieties may be a part of an assay designed to take advantage of improved sensitivity available from use of haptens and competitors set forth herein. These detectable moieties can be bound to the antibodies or competitors of the present invention. Of the preferred enzymatic methods for determination, one particularly preferred method involves an ELISA technique.

One assay procedure that may be used for the analysis of samples containing PCBs is one in which antibodies are immobilized on the walls of a plastic support (test tubes or plastic wells). This immobilization can be either direct or through an immobilized anti-mouse antibody, anti-rabbit antibody, and the like. In such an assay procedure the standards and test samples are mixed with a limited amount of competitor conjugated directly to an enzyme, such as alkaline phosphatase or horseradish peroxidase. The free compound (PCB analyte) in the sample competes with the enzyme conjugate for binding to the immobilized antibody. Enzyme substrate and chromogen are added for color development by the bound enzyme. The intensity of the color is inversely proportional of the amount of PCB content. See, e.g., A. Voller, "Heterogenous Enzyme Immunoassays and their Applications", *Enzyme Immunoassay*, CRC Press, p. 183 (1980).

The first step in one preferred embodiment of the assay process is to immobilize a competitor on a solid support, such as a plastic surface (e.g., inside a plastic test tube or in the well of a microtiter plate). After the competitor is immobilized, the support is washed to remove the unbound material. Simple adsorption is generally sufficient for the immobilization, particularly if the competitor is in the form of a competitor-protein complex.

In the second step, a sample containing the analyte (PCBs) is added in solution either from a standard or as part of the sample being analyzed. The antibody is then added. When no PCB is in the solution, a maximum amount of antibody binds to the competitors on the plate. A high concentration of PCBs in solution blocks binding of the antibody to the competitors bound to the plate. At intermediate PCB concentrations, some antibody will be bound to the competitors and some will remain in solution. At the end of the incubation period, the solution phase is washed away, leaving behind that fraction of the antibody that is bound to the immobilized competitor. The competitors are preferably a competitor of Formula I or II above, more preferably Formula I, and most preferably one of the exemplified competitors below.

The final step in the preferred assay is the detection of the antibody which remains bound to the competitors. This is done by detecting enzymatic activity associated with the antibody. The enzyme can either have been directly conjugated to the hapten specific antibody used in the second step or introduced via an enzyme conjugated second antibody that binds to the anti-hapten antibody. A wide variety of enzymes and substrates are suitable. Enzymatic activity is most often demonstrated by the release of a colored product that can be detected spectrophotometrically.

In addition to these EIA protocols, reagents of the present invention will be usable in the development of a variety of assay formats. Examples include fluorescence, chemiluminescence, and luminescence methods, dipsticks and other rapid test devices for semi-quantitative use, fluorescence sensors, electrodes, and other sensor devices. Also, the reagents of the present invention, i.e., competitors and haptens, may be used in the method described in EP 0455 058 A2, which is incorporated herein by reference.

Haptens

Haptens are used to produce antibodies for use in the assays of the present invention. A suitable hapten is conjugated with a carrier protein and injected into an animal (e.g. mice, rabbits, goats, horses) to induce an immune response. Suitable carrier proteins include keyhole limpet hemocyanin (KLH); bovine serum albumin (BSA), egg ovalbumin, thyroglobulin, bovine gamma globulin, and others known in the art (e.g., U.S. Pat. No. 4,456,691, incorporated herein by reference). The haptens of the present invention may be complexed with, or conjugated to, a carrier protein using a variety of methods known to those skilled in the art.

Suitable haptens include those having the general Formula III, as discussed above. Novel haptens that are useful in the production of antibodies for use in the present invention include those haptens of Formula III wherein L is —S—, or —CH$_2$—. Examples of suitable haptens include Exemplary Haptens I–VI (n=1–30):

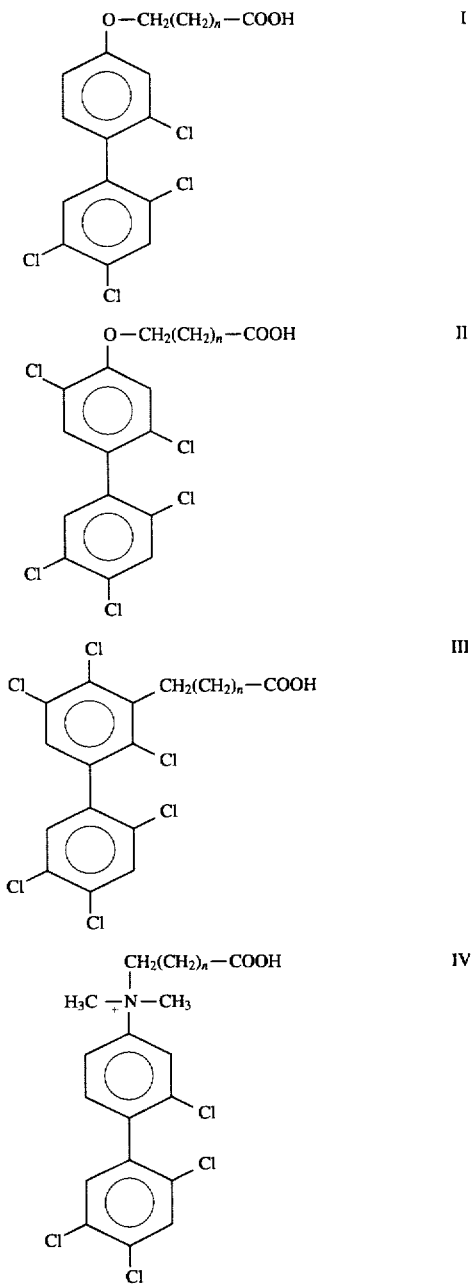

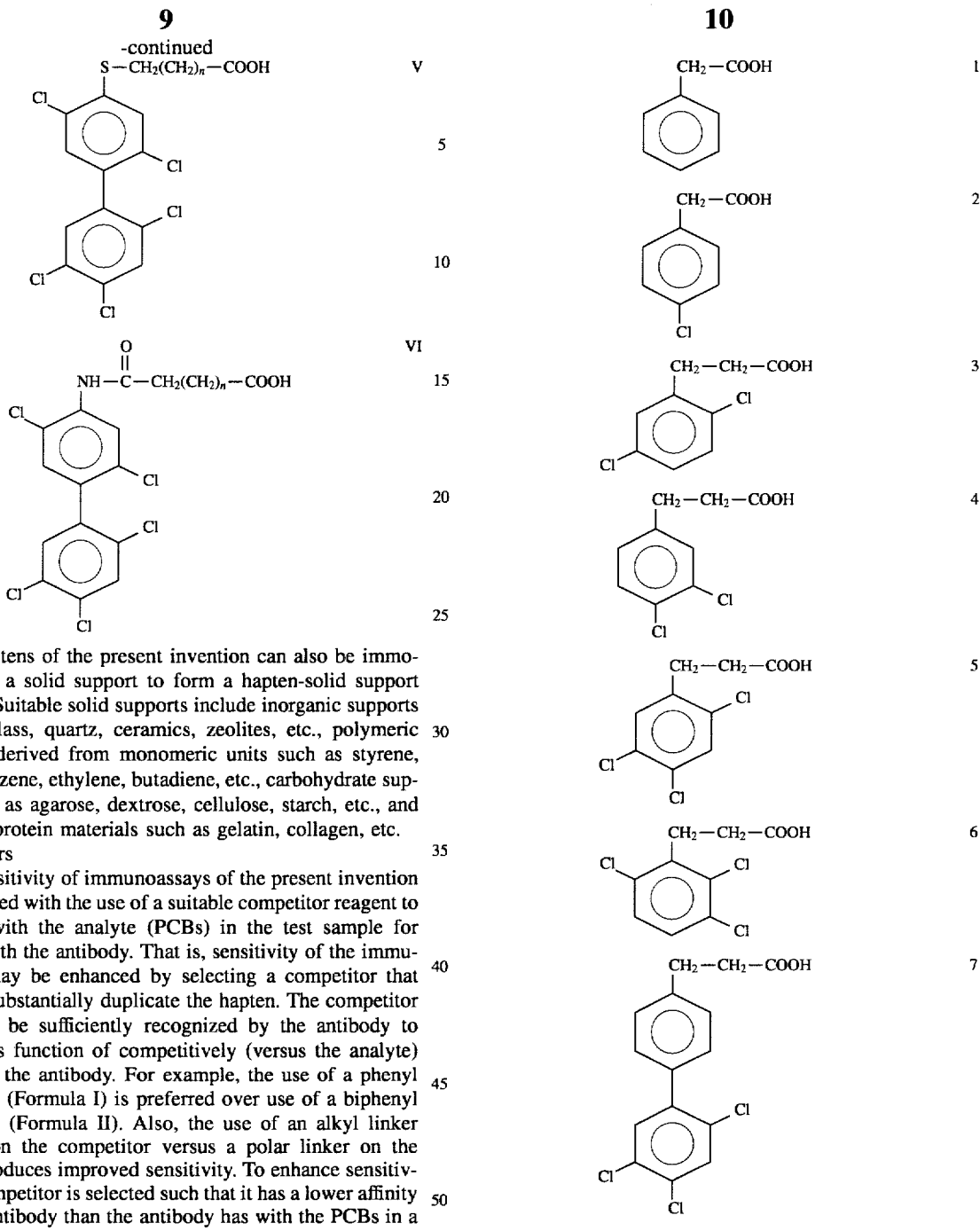

The haptens of the present invention can also be immobilized on a solid support to form a hapten-solid support complex. Suitable solid supports include inorganic supports such as glass, quartz, ceramics, zeolites, etc., polymeric materials derived from monomeric units such as styrene, divinylbenzene, ethylene, butadiene, etc., carbohydrate supports such as agarose, dextrose, cellulose, starch, etc., and insoluble protein materials such as gelatin, collagen, etc.

Competitors

The sensitivity of immunoassays of the present invention are enhanced with the use of a suitable competitor reagent to compete with the analyte (PCBs) in the test sample for binding with the antibody. That is, sensitivity of the immunoassay may be enhanced by selecting a competitor that does not substantially duplicate the hapten. The competitor must only be sufficiently recognized by the antibody to perform its function of competitively (versus the analyte) binding to the antibody. For example, the use of a phenyl competitor (Formula I) is preferred over use of a biphenyl competitor (Formula II). Also, the use of an alkyl linker (A-B-C) on the competitor versus a polar linker on the hapten, produces improved sensitivity. To enhance sensitivity, the competitor is selected such that it has a lower affinity with the antibody than the antibody has with the PCBs in a test sample. The relative affinity of a particular antibody or antisera for the analyte versus a particular competitor can be measured using, for example, equilibrium dialysis. The most common format for this evaluation would utilize a solution of the antibody to which was added either $^{14}$C-labeled Aroclor® 1248 or a particular $^{14}$C-labeled congener (e.g., 2,2',4,4'5,5'-hexachlorobiphenyl) either alone or in competition with a competitor. Competitors of the present invention will have one of the general structures of Formulas I or II above. Preferred competitors include Exemplary Competitors 1–11:

-continued

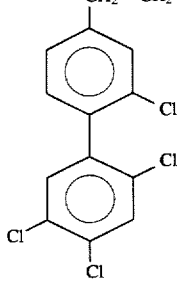
8

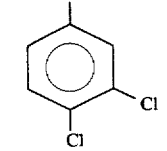
9

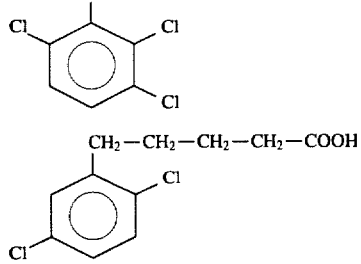
10

11

The competitors of the present invention can be bound to proteins. Suitable proteins for binding to the competitors include keyhole limpet hemocyanin (KLH); bovine serum albumin (BSA), egg ovalbumin, thyroglobulin, bovine gamma globulin, and others known in the art (e.g., U.S. Pat. No. 4,456,691, incorporated herein by reference). The competitors of the present invention may be complexed with, or conjugated to, a carrier protein using a variety of methods known to those skilled in the art.

The competitor is preferably used in a labeled or immobilized format. That is, preferably the competitor is labeled with a detectable moiety, such as an enzyme, radioisotope, chemiluminescent molecule, fluorescent molecule, luminescent molecule, or other detectable moiety known in the art. The competitor can also be immobilized on a solid support to form a competitor-solid support complex. Suitable solid supports include inorganic supports such as glass, quartz, ceramics, zeolites, etc, polymeric materials derived from monomeric units such as styrene divinylbenzene, ethylene, butadiene, etc., carbohydrate supports such as agarose, dextrose, cellulose, starch, etc., and insoluble protein materials such as gelatin, collagen, etc.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXAMPLES

General Experimental Procedures

NMR spectra were recorded with Nicolet NT-300 or IBM 200 MHz instruments. Mass spectral data were obtained with an AEI-ms 30 spectrometer. Gas chromatography (GC) was performed on a HP 5890, equipped with an FID detector under the following conditions: hold 2 minutes, 100°–275° C., 15° C./min. A 30 m×0.32 mm I.D. Supelco SPB-5, 0.25 μm film thickness (5% diphenyl: 94% dimethyl: 1% vinyl polysiloxane phases) column was used for all GC analyses. Flash as well as medium pressure liquid chromatography (MPLC) were carried out with hand packed 40 μm Baker silica gel columns. Thin layer chromatography (TLC) was done on 250 μm silica gel GF Uniplates.

Competitor Synthesis

The competitors are readily available from commercial sources (for example, 3-(3,4-dichlorophenyl)propionic acid (Exemplified Competitor 9) (Aldrich) or by the addition of a linker to the appropriate polychlorotoluene (for example, Exemplified Competitor 11).

Hapten Synthesis

The haptens (Exemplified Haptens I–VI) can be prepared using known synthetic strategies.

Example 1

METHOD A: Titer Determination

A solution of the coating antigen, consisting of 100 ng of a BSA conjugate of Hapten I or Exemplified Competitor 11 above, in 50 μL of PBS (phosphate buffered saline, pH 7.4, 10 mM phosphate, 150 mM NaCl), was dispensed into each well of a 96-well microtiter plate (Dynatech Immulon-2 commercially available from Dynatech, Inc., Chantilly, Va.) and incubated at 28° C. (+/−0.5° C.) for 2 hours. The coating antigen solution was then removed from the wells and the plate was washed three times with PBS. All wash steps utilized a Cambridge Technology, Inc. Platewasher 260, commercially available from Cambridge Technology, Inc. Cambridge, Mass. The remaining active sites in the wells were blocked with a 150 μL solution of 1% BSA in PBS with 0.02% sodium azide for 2 hours at 28° C. After removal of the blocking solution the plate was washed three times with PBS. Serum stored at −20° C. was freshly thawed and diluted 100–250,000 fold with the 1% BSA in PBS/DT blocking buffer (PBS buffer containing 10% by volume dimethylformamide and 0.5% Triton X-100). This solution (50 μl/well) was then dispensed into replicate wells (3–6) on the plate, which was covered and incubated for 1 hour at room temperature (RT). After removal of the incubation solution the plate was washed three times with PBS. The labeled antibody, anti-rabbit IgG (whole molecule)-alkaline phosphatase conjugate, (Sigma No. A-8025 commercially available from Sigma Chemical Company, St. Louis, Mo.), diluted 1/500 with BSA/PBS, was added in a quantity of 50 μl/well and incubated for 1 hour at 28° C. After removal of the second antibody solution the plate was washed three times with PBS. The wells were then washed (one time) with 10 mM diethanolamine (pH 9.4) which contained 0.5 mM magnesium chloride. Substrate solution (50 μl; 10 mg p-nitrophenylphosphate in 10.0 ml of the diethanolamine/magnesium chloride) was added to each well and incubated for 30 minutes at 28° C. Sodium hydroxide (50 μl of a 0.05N solution) was added to each of the wells to stop the reaction. The final Absorbance in each well was determined at 405 nm using a Cambridge Technologies, Inc. Model 750 Microplate Reader commercially available from Cambridge Technologies, Inc., Cambridge, Mass. The titer of the sera was determined by a Log Sera Dilution versus Absorbance plot and the EC50 value.

Example 2

METHOD B: Inhibition ELISA

Inhibition ELISA followed the basic assay procedure described above with the following addition: The serum sample was diluted to its EC80 value (400–1000 fold) with the 1% BSA in PBS blocking buffer to which had been added 10% dimethylformamide, volume/volume (v/v), and 0.5% Triton® X-100 (PBS-DT). An aqueous analyte solution (e.g., Aroclor® 1248) was prepared by solution of the analyte in dimethylformamide followed by dilution to the required concentration in PBS-DT. The analyte solution was added to the antibody solution to achieve the desired concentration of analyte (typically 1 ppb–100 ppm) and the resulting solution was incubated overnight at room temperature. This solution (50 μl/well) was then dispensed into replicate wells (3–6) on the plate and the assay completed as above. The minimum detection limit ($I_{10}$) and the $I_{50}$ values were determined using a Log (Analyte Concentration in parts per billion–ppb) versus Absorbance or by converting absorbance to the B/Bo ratio where B=Sample Absorbance and Bo=Absorbance of the Blank Sample. FIG. 1 includes plot 1 for Hapten I and plot 3 for Competitor 11 demonstrating the improved sensitivity using a competitor of the invention. This figure illustrates the significant improvement in PCB sensitivity as measured by both minimum detection limit (B/Bo=0.9) and assay range (B/Bo=0.5) on using a competitor versus a hapten as the competition reagent.

Example 3

METHOD C: Soil Extract Preparation 1 ×DMF Method 1.0 grams of soil is weighed out and placed into a glass vial with a teflon-lined screw cap. 1.0 ml of dimethylformamide (DMF) is added and the sample is rocked gently overnight at room temperature. The samples are centrifuged at approximately 1000 × G for 10 minutes and the supernatant is removed and transferred to a clean vial.

Example 4

Synthesis of Hapten I

Figure 2:
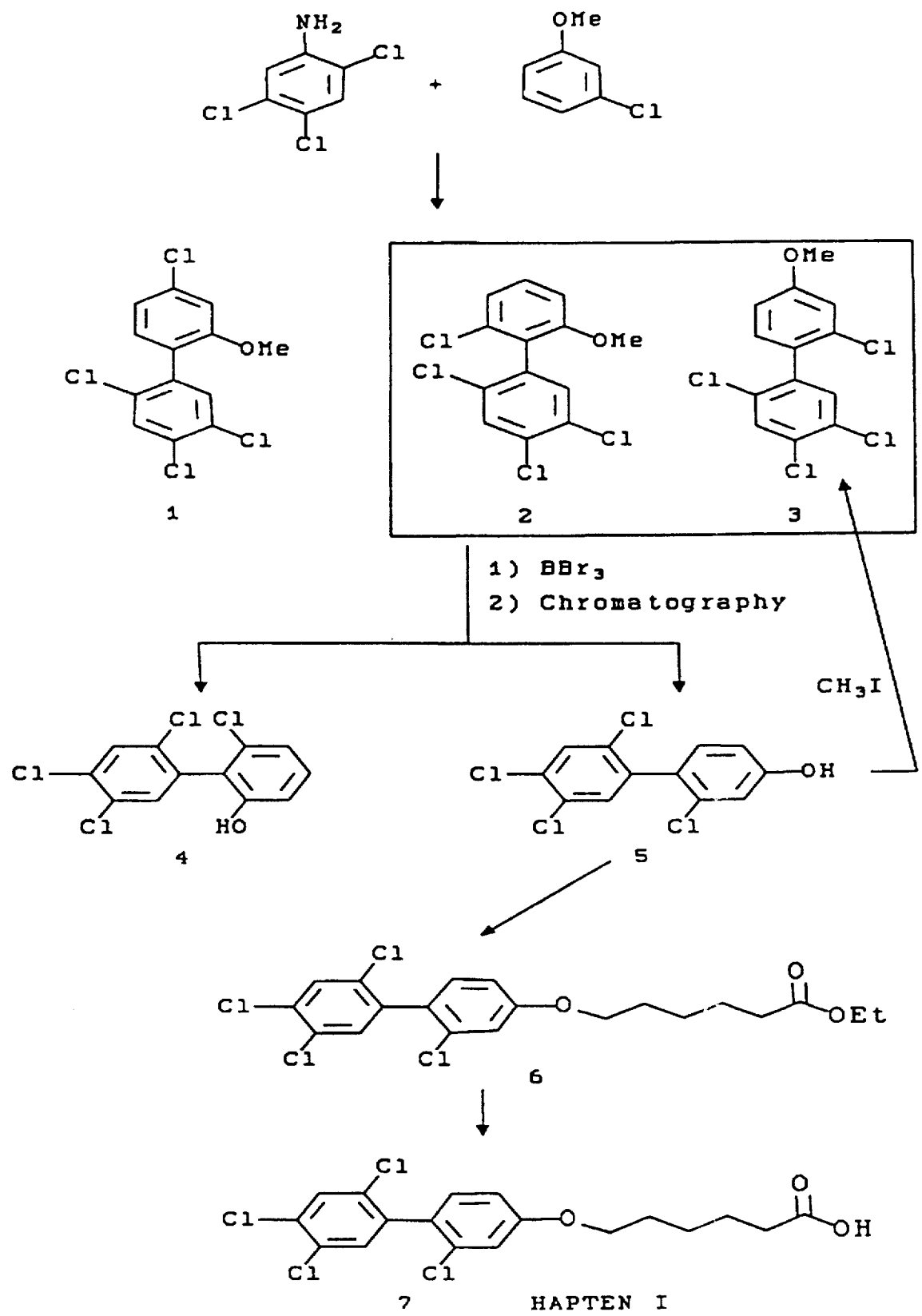
FIG. 2 is a schematic of the synthesis of a preferred hapten.

Hapten I was prepared as shown in FIG. 2. The methoxy biphenyls (1, 2, and 3) were the result of a Cadogen coupling of 2,4,5-trichloroaniline and 3-chloroanisole. J.I.G. Cadogen, *J. Chem Soc.*, C (1966) 1249. Upon distillation of unreacted anisole, isomer 1 was readily separated from the crude product via flash chromatography. Isomers 2 and 3, obtained as a mixture which was difficult to resolve, were carried into $BBr_3$ demethylation. The resulting biphenylols 3 and 5 were easily resolved by flash chromatography. The positional substitutions of biphenyls 1 and 5 could not be unequivocally differentiated from their NMR spectra because of the expected similar coupling patterns. In order to further establish their structures, nuclear overhauser enhancement (NOE) experiments were performed on methyl ethers 1 and 3. The latter was obtained in pure form by reaction of 5 with methyl iodide. In the case of isomer 1, irradiation of the methyl ether signal produced an enhancement of the resonance for the single adjacent proton (H-3) in the difference spectrum. In contrast, irradiation of the methyl ether signal of compound 3 revealed NOE's to the two adjacent protons (H-3 and H-5), thus establishing the desired configuration present in 3 and 5. Biphenylol 5 was alkylated with ethyl 6-bromohexanoate to yield the ethyl ester 6. Upon isolation of the pure precursor, hapten I (7) was prepared by LiOH hydrolysis of 6 at room temperature.

2,2',4',5'-Tetrachloro-4-methoxybiphenyl

Isoamyl nitrite (18.8 mL, 0.140 mol) was added portionwise over the course of 1 hour to a mixture of 3-chloroanisole (100 g, 0.70 mol) and 2,4,5-trichloroaniline (13.75 g, 0.070 mol) at 120° C. under nitrogen and the reaction was allowed to stir an additional 18 hours, and then distilled (0.2 mmHg, 160°–185° C.) to yield 14.07 g (62%). A 300 mg portion of the distillate was further purified via flash chromatography (silica gel, hexane eluent). Fraction 1 (32.2 mg, Rf=0.33; GC RT=14.44 minutes) was identified as 2',4,4',5'-tetrachloro-2-methoxybiphenyl. Fraction 2 (75.2 mg, Rf=0.22) contained a mixture of two products in a 40:60 ratio. Through subsequent demethylation and separation, these were determined to be the 2,2',4',5'-tetrachloro-6-methoxy and 2,2',4',5'-tetrachloro-4-methoxybiphenyl derivatives (GC retention time=14.01, 14.69 minutes respectively).

2',4,4',5'-tetrachloro-2-methoxybiphenyl (fraction 1): $^1$H-NMR (300 MHz CDCl$_3$) δ=7.56 (s, H3'), 7.35 (s, H6'), 7.08 (d, J=8.1 Hz, H6), 7.01 (dd, J=1.6, 8.0 Hz, H5), 6.96 (d, J=1.4 Hz, H3), 3.78 (s, OCH$_3$).

MS (EI), m/e (relative intensity) 320 (M, 38), 270 (22), 250 (8), 28 (100); exact mass calculated for $C_3H_8OCl_4$, [M]$^+$319.9327, found 319.9343.

2,2',4',5'-Tetrachloro-4-hydroxybiphenyl 1.0M BBr$_3$ (3.56 mL, 3.56 mmol) in CH$_2$Cl$_2$ was added to the mixture of 2,2',4',5'-tetrachloro-4-methoxy and 2,2',4',5'-tetrachloro-6-methoxybiphenylderivatives (731mg, 2.27 mmol) in 15 mL CH$_2$Cl$_2$ and the reaction was allowed to stir for 36 hours, then quenched by the addition of 5 mL saturated KH$_2$PO$_4$. The reaction mixture was diluted with diethyl ether and washed with several portions of KH$_2$PO$_4$, water and brine. The organic layer was dried with anhydrous Na$_2$SO$_4$, filtered and concentrated to a dark oil. The crude product was purified via flash chromatography (silica gel, 60/40, hexane/benzene eluent). Fraction 1 (327 mg, 47%; Rf=0.31; GC retention time=14.20 minutes) was identified as 2,2',4',5'-tetrachloro-6-hydroxybiphenyl. Fraction 2 (229 mg, 33%; Rf-0.25; GC RT=15.55 minutes) was found to be 2,2',4',5'-tetrachloro-4-hydroxybiphenyl.

2,2',4',5'-tetrachloro-6-hydroxybiphenyl (fraction 1): $^1$H-NMR (300 MHz, CDCl$_3$) δ=7.67 (s, H3'), 7.41 (s, H6'), 7.25 (dd, J=6.5, 8.2 Hz, H4), 7.09 (dd, J=0.96, 7.9 Hz, H3), 6.88 (dd, J=0.94, 8.3 Hz, H5), 4.80 (s, OH).

MS (EI), m/e (relative intensity) 306 (M, 78), 270 (18), 236 (100), 207 (15), 173 (16), 103 (18), 28 (100); exact mass calculated for $C_{12}H_6OCl_4$, [M]$^+$ 305.9171, found 305.9182.

2,2',4',5'-tetrachloro-4-hydroxybiphenyl (fraction 2): $^1$H-NMR (300 MHz, CDCl$_3$) δ=7.58 (s, H3'), 7.37 (s, H6'), 7.10 (d, J=8.4 Hz, H6), 6.99 (d, J=2.5 Hz, H3), 6.81 (dd, J=2.5, 8.3 Hz, H5), 5.19 (s, OH).

MS (EI), m/e (relative intensity) 308 (100), 306 (80), 236 (45), 207 (15), 173 (18), 43 (22), 28 (72); exact mass calculated for $C_{12}H_6OCl_4$, [M]$^+$ 307.9908, found 307.9168.

Ethyl 6-(2,2',4',5'-tetrachlorobiphenyloxy)-4-yl hexanoate

Ethyl 6-bromohexanoate was added to a solution of 2,2',4',5'-tetrachloro-4-hydroxybiphenyl (81.7 mg, 0.266 mmol) in N,N-dimethylformamide. Anhydrous K$_2$CO$_3$ (140 mg, 1.01 mmol) and NaI (5 mg, 0.003 mmol) were added to the vigorously stirred mixture. The reaction mixture was allowed to stir at 130° C. under nitrogen for 5 hours. The reaction was cooled to room temperature, then diluted with 50 mL diethyl ether. The resulting organic solution was washed with five portions of water and once with brine. The organic layer was dried with anhydrous $Na_2SO_4$, filtered and concentrated to 125 mg (97%) of a light yellow oil.

$^1$H-NMR (300 MHz, $CDCl_3$) δ=7.57 (s, H3'), 7.36 (s, H6'), 7.11 (d, J=8.5 Hz, H6), 7.00 (d, J=2.5 Hz, H3), 6.85 (dd, J=2.5, 8.5 Hz, H5), 4.14 (q, J=7.2 Hz, $COOCH_2CH_3$), 3.99 (t, J=6.4 Hz, Ar—OO $CH_2$—), 2.34 (t, J=7.3 Hz, —$CH_2CH_2COOCH_2CH_3$), 1.83 (quintet, J=7.1 Hz, Ar—O—$CH_2CH_2CH_2$—), 1.72 (quintet, J=6.7 Hz, —$CH_2CH_2CH_2COOCH_2CH_3$), 1.54–1.49 (m, Ar—O—$CH_2CH_2CH_2$—), 1.26 (t, J=7.1 Hz, —$COOCH_2CH_3$).

MS (EI), m/e (relative intensity) 448 (M, 7), 306 (23), 236 (10), 143 (100), 97 (67), 69 (75), 55 (18), 28 (45); exact mass calculated for $C_{20}H_{20}O_3Cl_4$, [M]$^+$ 448.0165, found 448.0134.

6-(2,2',4',5'-Tetrachlorobiphenyloxy)-4-yl hexanoic acid

500 µL methanol was added to a solution of ethyl 6(2,2', 4',5'-tetrachlorobiphenyloxy)-4-yl hexanoate (120 mg, 0.248 mmol) in 500 µL tetrahydrofuran. The resulting solution was added to 1 mL 30% KOH and heated in a sealed tube, with stirring for 2 hours. The reaction was cooled to room temperature and allowed to stir for an additional 18 hours. The reaction mixture was diluted with 1M HCl and extracted with several portions of diethyl ether. The combined organic layers were dried with anhydrous $Na_2SO_4$, filtered and concentrated to a heavy oil. The crude product was purified via flash chromatography (silica gel, 9:1, hexane/ethyl acetate, containing 1% acetic acid) to yield 93 mg (88%, Rf=0.30) of a water white oil.

$^1$H-NMR (300MHz, $CDCl_3$) δ=7.57 (s, H3'), 7.36 (s, H6'), 7.11 (d, J=8.6 Hz, H6), 7.01 (d, J=2.2 Hz, H3), 6.85 (dd, J=2.5, 8.6 Hz, H5), 3.99 t, J=6.2 Hz, Ar—O—$CH_2CH_2CH_2$—), 2.41 (t, J=7.3 Hz, —$CH_2CH_2CH_2COOH$), 1.86–1.79 (m, Ar—O—$CH_2CH_2CH_2$—), 1.76–1.69 (m, —$CH_2CH_2CH_2COOH$), 1.60–1.52 (m, Ar—O—$CH_2CH_2CH_2$—).

MS (EI), (relative intensity) 422 (20), 420 (15), 308 (100), 306 (70), 236 (20), 97 (25), 55 (15), 28 (15); exact mass calculated for $C_{18}H_{16}O_3Cl_4$, [M]$^+$ 419.9872, found 419.9861.

Example 5

Hapten I Conjugation

Hapten I was conjugated to the carrier proteins keyhole limpet hemocyanin and bovine serum albumin through a carbodiimide mediated carboxyl activation procedure. Control reactions which contained hapten and protein without the activating reagent were used to evaluate the efficiency of the aqueous dioxin dialysis procedure for removal of non-covalent (vida infra) hapten from the conjugate solution. Hapten loads could not be accurately assessed using a differential UV/V is procedure. Consequently, a procedure for the release of the hapten from the conjugate through amide hydrolysis was developed. The released hapten was subsequently quantified by GC. The following conjugates were prepared:

| Sample | GC Load | Quantity |
| --- | --- | --- |
| KLH Hapten I Conjugation | 49 | 19 mg |
| KLH Hapten I Control | 0.8 | |
| BSA Hapten I Conjugation | 12 | 10 mg |
| BSA Hapten I Control | 1.9 | |

Hapten I, calculated to be a 200 fold excess over keyhole limpet hemocyanin (KLH) or a 100 fold excess over bovine serum albumin (BSA) was dissolved in 0.1 mL dimethylformamide (Aldrich, gold label) and preactivated to form the N-hydroxyl succinimide (NHS) ester. The activation was carried out using a 2 fold molar excess (calculated over the hapten) of 1-ethyl-3-[3-dimethylaminopropyl]carbodiimide (EDC) and a 2 fold molar excess (also calculated over the hapten) of NHS added dry to the hapten solution.

The carrier protein was dissolved in borate buffer (0.1M, pH 9.4) to a final concentration of 10 mg/mL. The protein solution was allowed to stir overnight at 0°–5° C. to ensure that all of the protein was dissolved. Dimethylformamide (Aldrich, gold label) was added to a concentration of 5% (v/v). The preactivated hapten solution was added to the protein solution, 10 µL at a time, every 15 minutes, using a 10 µL Hamilton syringe. The BSA conjugation solution routinely became turbid with each addition and remained slightly turbid throughout the whole process. The KLH conjugation solution routinely became turbid with each addition, but became clear upon stirring. The conjugation mixtures were allowed to stir for an additional hour at room temperature and then overnight at 0°–5° C.

Samples were transferred to wetted cellulose dialysis tubing (mw cutoff 12,000–14,000) and dialyzed vs. 1.0 L volumes of 25% dioxane (EM Science, glass distilled) in phosphate buffered saline (PBS, pH 7.4) for two days, changing to fresh dialysate buffer after the first day. Controls containing no EDC showed that this method was successful in removing any nonspecifically bound hapten from the carrier protein.

Samples were dialyzed vs. 1.0 L volumes of PBS for two days to remove any traces of dioxane, changing to fresh PBS after the first day. After dialysis, samples were centrifuged at 1000× G for 10 minutes at 0°–5° C. to remove any precipitate.

Load Determination

The moles of carrier protein were determined by the Lowry method with the use of an appropriate protein standard curve. The moles of hapten were determined by hydrolysis of the conjugates to liberate the hapten for quantitation by GC.

Conjugates were hydrolyzed in 6N HCl in an evacuated, sealed ampule for 18 hours at 110° C. After cooling to room temperature, the hapten was extracted from the acid solution with ethyl acetate (3×500 µL). The combined extracts were dried by passage through a small column of anhydrous $Na_2SO_4$ and then concentrated under reduced pressure. The extracted hapten was converted to the methyl ester using $CH_2N_2$ and then concentrated to a dry residue. The residue was dissolved in 100 µL of ethyl acetate and analyzed by GC using the following conditions: Retention time: 19.1 minutes Column: 30 m×0.32 mm I.D. Supelco SPB-5, 0.25 µm film thickness (5% diphenyl: 94% dimethyl: 1% vinyl polysiloxane phases). Column temp.: 275° C. Instrument: HP 5890, FID detector The hapten was quantified by comparing the peak areas to the appropriate hapten standard curve. The conjugate load was determined by dividing the moles of hapten present by the moles of carrier protein.

Example 6

Hapten II Synthesis

Figure 3:
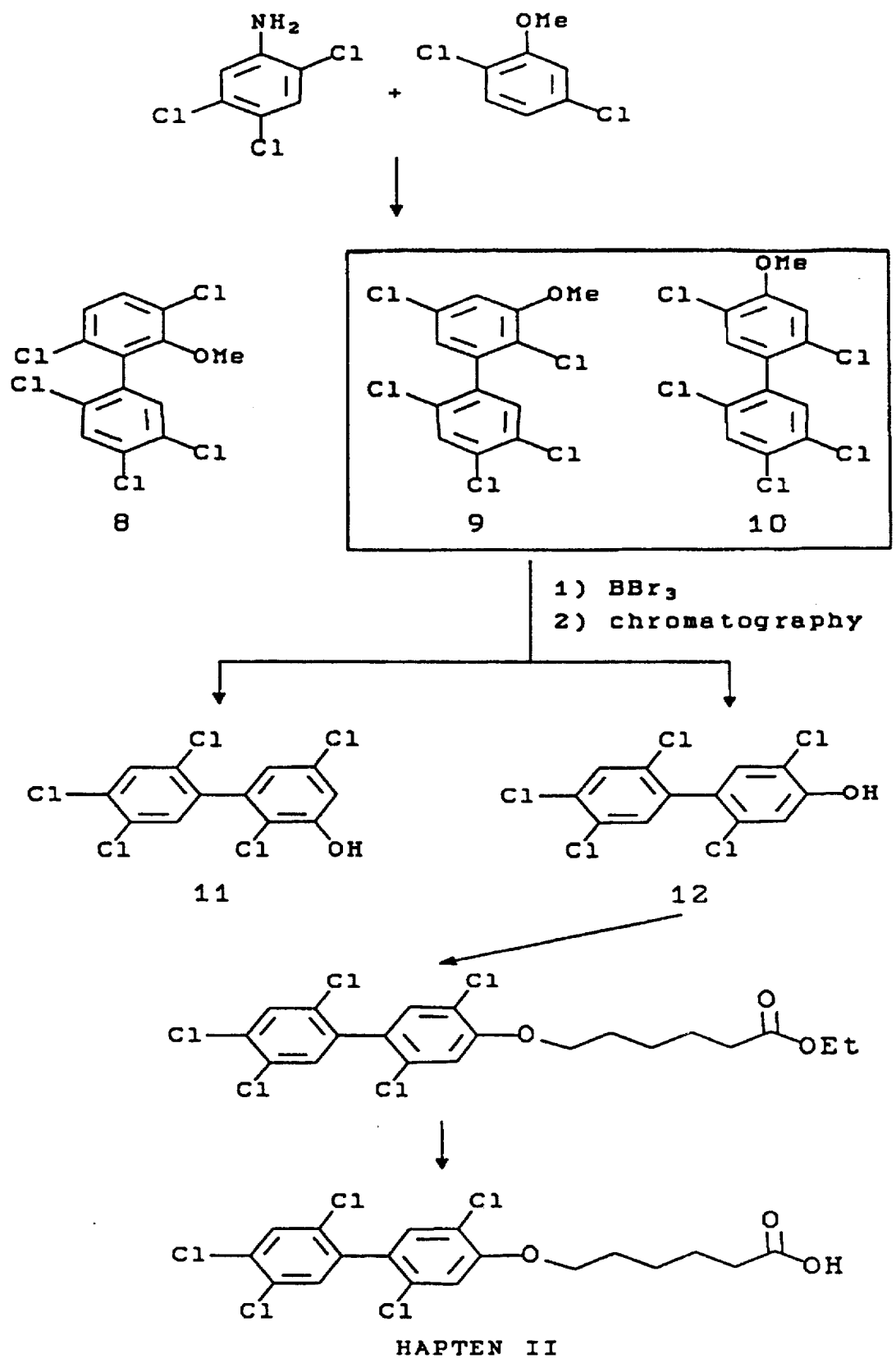
FIG. 3 is a schematic of the synthesis of a second preferred hapten.

Hapten II was prepared as shown in FIG. 3. The requisite 2,5-dichloroanisole was prepared by alkylation of the corresponding phenol with methyl iodide. Methyl ethers 8, 9, and 10 were obtained from a two-phase coupling reaction where the trichloroaniline was diazotized under aqueous conditions and added to a $CCl_4$ solution of dichloroanisole, then neutralized with saturated sodium acetate. Goldstien, J. A., *Chem.-Biol. Interactions*, 17, 69–87 (1977). Isomer 8 was readily separated via flash chromatography while isomers 9 and 10 were only separable upon $BBr_3$ demethylation. The structures of biphenylols 11 and 12 were unambiguously assigned due to their unique proton NMR spectra. Alkylation and subsequent hydrolysis followed that of the Hapten I scheme.

2,5-Dichloroanisole

Anhydrous $K_2CO_3$ (21.9 g, 0.159 mol) and methyl iodide (10.8 mL, 0.178 mol) were added to a solution of 2,5-dichlorophenol (23.5 g, 0.144 mol) in 215 mL acetone. The reaction was allowed to stir at room temperature for 20 hours, then filtered through a celite pad. The filtrate was concentrated to a residue which was taken up in diethylether. The ether solution was washed with 10% $NaHSO_3$, water, several portions of 1M NaOH, and brine, then dried with anhydrous $Na_2SO_4$. Upon filtration and concentration, the residue was distilled (8 mm Hg, 110° C.) to yield 23.7 g (93.5%) of a light yellow oil.

$^1$H-NMR (200MHz, $CDCl_3$) δ=7.27 (d, J=9.2 Hz, H3), 6.91 (br s, H6), 6.78 (dd, J=2.2, 8.0 Hz, H$_4$), 3.89 (s, OC$\underline{H}_3$).

2,5,2',4',5'-Pentachloro-4-methoxybiphenyl

To a suspension of 2,4,5-trichloroaniline (1.96 g, 10 mmol) in 30 mL 35% $H_2SO_4$ in an ice/salt bath (below 0° C.) was added a solution of sodium nitrite (0.828 mg, 12 mmol) in 50 ml cold distilled water. The yellow mixture was allowed to stir below 0° C. for 45 minutes at which time it was added to a vigorously stirred solution of 2,5-dichloroanisole (1.76 g, 10 mmol) in 100 mL $CCl_4$ below 0° C. Saturated sodium acetate solution was added until a pH≧7 was obtained. The resulting mixture was allowed to warm to room temperature, then stirred 18 h. The reaction was extracted with several portions of $CH_2Cl_2$ and the combined organic layers were dried with anhydrous $Na_2SO_4$, filtered, then concentrated to a heavy oil. The oil was distilled (150°–200° C., 0.2 mm Hg) through a Kugelrhor apparatus to yield 0.8 g of a dark yellow oil. The distillate was further purified via flash chromatography (silica gel, hexane eluent). Fraction 1 (40 mg; Rf=0.38; GC retention time=16.32 minutes) was identified as 2,2',4',5,5'-pentachloro-6-methoxybiphenyl. Fraction 2 (262 mg, 7.4% yield; Rf=0.33) was found to contain 2,5,2',4',5'-pentachloro-3-methoxy and 2,5, 2',4',5'-pentachloro-4-methoxybiphenyl in a 17:83 ratio as determined by GC (RT=17.58, 17.75 minutes respectively) and NMR analyses.

2,2',4',5,5'-Pentachloro-6-methoxybiphenyl (fraction 1):H-NMR (300MHz, $CDCl_3$) δ=7.54 (s, H3'), 7.31 (d, J=8.7 Hz, H4), 7.16 (s, H6'), 7.12 (d, J=8.8 Hz, H5), 3.52 (s, $OCH_3$).

2,5,2',4',5'-Pentachloro-3-methoxybiphenyl (fraction 2, minor component): $^1$H-NMR (300MHz, $CDCl_3$) δ=7.59 (s, H3'), 7.34 (s, H6'), 6.98 (d, J=2.2 Hz, H6), 6.85 (d, J=2.2 Hz, H6), 3.89 (s, $OCH_3$).

2,5,2',4',5',-Pentachloro-4-methoxybiphenyl (fraction 2, major component): $^1$H-NMR (300MHz, $CDCl_3$) δ=7.59 (s, H3'), 7.36 (s, H6'), 7.26 (s, H6), 7.03 (s, H3) 3.95 (s, $OCH_3$).

2,5,2',4',5'-Pentachloro-4-hydroxybiphenyl

To a mixture of 2,5,2',4',5'-pentachloro-4-methoxy and 2,5,2',4',5'-pentachloro-3-methoxybiphenyl (1.00 g, 2.8 mmol) in 15 mL $CH_2Cl_2$ was added 1.0M $BBr_3$ (4.21 mL, 4.21 mmol) in $CH_2Cl_2$. The reaction was allowed to stir for 36 hours, then quenched by the addition of 6 mL saturated $KH_2PO_4$. The reaction mixture was diluted with diethyl ether and washed with several portions of 10% $KH_2PO_4$, water and brine. The organic layer was dried with anhydrous $Na_2SO_4$, filtered and concentrated to a dark oil. The crude product was partially purified by flash chromatography (silica gel, 19:1, hexane: ethyl acetate eluent, 854 mg, Rf=0.30), and then medium pressure liquid chromatography was performed on a 400 mg portion (silica gel, 30/70 benzene/hexane eluent). Fraction 1 (68 mg, 17.0%; Rf=0.31; GC retention time=16.86 minutes) was identified as 2,5,2', 4',5'-pentachloro-3-hydroxybiphenyl. Fraction 2 (50 mg 12.5%; Rf=0.28; GC RT=17.84 min) was found to be 2,5,2',4',5'-pentachloro-4-hydroxybiphenyl.

2,5,2',4',5'-pentachloro-3-hydroxybiphenyl (fraction 1): $^1$H-NMR (300MHz, $CDCl_3$) δ=7.60 (s, H3'), 7.36 (s, H6'), 7.12 (d, J=2.4 Hz, H6), 6.83 (d J=2.4 Hz H4), 5.77 (s, OH).

MS (EI), m/e (relative intensity) 342 (100), 340 (M, 63), 270 (11), 182 (13), 135 (15), 28 (64); exact mass calculated for $C_{12}H_5OCl_5$ [M]$^+$ 339.8799, found 339.8779.

2,5,2',4',5'-pentachloro-4-hydroxybiphenyl (fraction 2): $^1$H-NMR (300MHz, $CDCl_3$) δ=7.59 (s, H3'), 7.35 (s, H6'), 7.22 (s, H6), 7.17 (s, H3), 5.71 (br s, O$\underline{H}$).

MS (EI), m/e (relative intensity) 342 (100), 340 (41), 272 (32), 243 (20), 171 (12), 119 (36); exact mass calculated for $C_{12}H_5OCL_5$ [M]$^+$ 339.8783, found 339.8772.

Ethyl 6-(2,2',4',5,5'-pentachlorobiphenyloxy)-4-yl hexanoate

To a solution of 2,5,2',4',5'-pentachloro-4-hydroxybiphenyl (157 mg, 0.459 mmol) in 0.50 ml DMF was added ethyl 6-bromohexanoate (82 μL, 0.459 mmol). To the vigorously stirred reaction mixture was added anhydrous $K_2CO_3$(253 mg, 1.84 mmol) and NaI (5 mg, 0,003 mmol). The reaction mixture was allowed to stir at 130° C. under nitrogen for 5 hours. The reaction was cooled to room temperature, then diluted with diethyl ether. The resulting organic solution was washed with five portions of water, and once with brine. The organic layer was dried with anhydrous $Na_2SO_4$, filtered and concentrated to give 216 mg (98%) of a light yellow oil.

$^1$H-NMR (300MHz $CDCl_3$) δ7.58 (s, H3'), 7.35 (s, H6'), 7.24 (s, H6), 7.00 (s, H3), 4.13 (q, J=7.1 Hz, $COOCH_2CH_3$) 4.06 (t, J=6.3 Hz, Ar—O—$CH_2CH_2$—), 2.36 (t, J=7.2 Hz, —$CH_2CH_2COOCH_2CH_3$), 1.90 (quintet, J=7.1 Hz, Ar—O—$CH_2CH_2CH_2$—), 1.74 (quintet, J=7.8 Hz $CH_2CH_2CH_2COOCH_2CH_3$), 1.57 (apparent singlet, Ar—O—$CH_2CH_2CH_2$—), 1.26 (t, J=7.2 Hz, $COOCH_2CH_3$).

MS (EI) m/e (relative intensity) 342 (28), 340 (M, 18) 143 (100), 97 (78), 69 (54); 55 (23), 28 (58); exact mass calculated for $C_{20}H_{19}O_3Cl_5$ [M]$^+$ 481.9775, found 481.9768.

6-(2,2',4',5,5'-Pentachlorobiphenyloxy)-4-yl hexanoic acid

To a solution of ethyl 6-(2,2',4',5,5'-pentachlorobiphenyloxy)-4-yl hexanoate (216 mg, 0.446 mmol) in 2 mL each, methanol and tetrahydrofuran, was added 2 mL of 2N LiOH.

The reaction was allowed to stir at room temperature for 18 hours. The organic solvents were removed under reduced pressure and the reaction mixture was acidified with 1N HCl. The milky suspension was extracted with several portions of $CH_2Cl_2$, and the combined organic extracts were dried with anhydrous $Na_2SO_4$ and then concentrated to a light yellow oil. The crude product was purified by flash chromatography ( silica gel, 19: 1, hexane: ethyl acetate with 1% acetic acid eluent) to yield 178 mg (87%) of a water white oil.

$^1$H-NMR (300MHz, $CDCl_3$) δ=7.60 (s, H3'), 7.37 (s, H6'), 7.27 (s, H6) 7.02 (s, H3), 4.08 (t, J=6.1 Hz, Ar—O—$CH_2CH_2$—), 2.44 (f, J=7.3 Hz, —$CH_2CH_2COOH$), 1.94–1.80 (m, Ar—O—$CH_2CH_2CH_2$—), 1.79–1.66 (m, —$CH_2CH_2CH_2COOH$), 1.63–1.58 (m, Ar—O—$CH_2CH_2CH_2$—).

MS (EI), m/e (relative intensity) 456 (18), 454 (10), 342 (100), 340 (60), 270 (20), 115 (73), 97 (50), 69 (85), 41 (48); exact mass calculated for $C_{18}H_{15}Cl_5O_3$, [M$^+$] 453.9464, found 453.9489.

Example 7

Hapten II Conjugation

Hapten II was conjugated to the carrier proteins Keyhole limpet hemocyanin and bovine serum albumin using the carbodiimide mediated carboxyl activation procedure described for Hapten I. Two significant problems were encountered during the preparation of the Hapten II conjugates: 1) nonspecific hapten sorption to the protein, as assessed by control reactions; and 2) control hapten recoveries through the amide hydrolysis were variable (30–120%). The first problem was ultimately solved through the use of an aqueous dioxane G-25 gel chromatography conjugate purification step. The second was solved through the repetitive use of parallel controls for definition of a recovery range. The following conjugates were prepared:

| Sample | GC Load | Quantity |
| --- | --- | --- |
| KLH Hapten II Conjugation | 58 | 30 mg |
| KLH Hapten II Control | 0 | |
| BSA Hapten II Conjugation | 24 | 22 mg |
| BSA Hapten II Control | 0.9 | |

Hapten II conjugation followed the procedures for Hapten I conjugation through the dialysis step. After dialysis, controls containing no EDC showed that dialysis was successful in removing any nonspecifically bound hapten from the BSA but not the KLH sample.

The KLH sample was removed from the dialysis buffer and centrifuged at 1000× G for 10 minutes at 0°–5° C. to remove any precipitate. The sample was passed through a Sephadex G25 (Aldrich, 50–150 μ) column preequilibrated with 25% dioxane in PBS. 1.5 mL fractions were collected and pooled according to their absorbance at 280 nm. Controls containing no EDC showed that passing the KLH conjugate through the column successfully removed any nonspecifically bound hapten from the protein.

The KLH conjugate was transferred back into wetted cellulose dialysis tubing (mw cutoff 12,000–14,000), and both the BSA and KLH conjugates were further dialyzed for two days vs. 1.0 L volumes of PBS, changing to fresh PBS after the first day. After dialysis, samples were centrifuged at 1000× G for 10 minutes at 0°–5° C. to remove any remaining precipitate. Load Determination Hapten II loads were determined as described for Hapten I.

Example 8

Exemplified Haptens I and II - ETHER LINK

Exemplified Haptens I and II can be prepared via Cadogen (J.I.G. Cadogen, *J. Chem. Soc.*, C 1249 (1966)) coupling of 2,4,5-trichloroniline and a suitable chloroanisole followed by isomer resolution, demethylation to the biphenylol and preparation of the linker moiety (see Examples 4 and 6).

Example 9

Exemplified Hapten III- ALKYL LINK

Exemplified Hapten III can be prepared via Cadogen coupling of 2,4,5-trichloroaniline and 2,3,5-trichlorotoluene followed by isomer resolution to give the methyl biphenyl derivative. Preparation of the linker moiety is based on reaction of the biphenyl methyl anion with an alkyl bromide linker (see, for example, the synthesis of Competitor 11).

Example 10

Exemplified Haptens IV and VI - AMINE and AMIDE LINK

Exemplified Haptens IV and VI can be prepared via nitration of the suitably substituted polychlorobiphenyl followed by isolation of the desired isomer and reduction to form the amino biphenyl derivative (see M. I. Luster, et al., *Toxicol. Appl. Pharmacol.*, 50, 147–155 (1979); and W. H. Newsome and J. B. Shields, *Intern. J. Environ. Anal. Chem.*, 10, 295–304 (1981)). The amine can be alkylated in a stepwise sequence to produce the quaternary linker or acylated to prepare the amide linker.

Example 11

Exemplified Hapten V - THIOETHER LINK

Exemplified Hapten V can be prepared in an analogous sequence to the ether haptens using a suitable chlorothioanisole precursor.

Example 12

Synthesis of Exemplified Competitor 11

The anion of 2,5-dichlorotoluene was reacted with trimethyl 4-bromoorthobutyrate to produce methyl 5-(2,5dichlorophenyl)pentanoate after hydrolytic work-up. Competitor 11 was prepared by LiOH hydrolysis of the methyl ester. Methyl 5-(2,5-dichlorophenyl)pentanoate Diisopropylamine (841 μl, 6 mmol) was added to 20 mL of THF under nitrogen atmosphere and cooled to 0° C. 5.5 ml of 2.5N n-butyllithium (55.5 mmol) was added and the reaction was stirred for 20 minutes. The reaction was then cooled to −78° C. 2,5-Dichlorotoluene (642 μL, 5 mmol) was added and stirring was continued for 2 hours at −78° C. Trimethyl 4-bromoorthobutyrate (1.14 g, 5 mmol) was added to the reaction mixture in 10 mL THF. The reaction was stirred for 5 minutes at −78° C., allowed to come to room temperature and stirred overnight. The reaction was worked-up by adding 10 mL of saturated $KH_2PO_4$, removal of most of the THF on a rotary evaporator followed by partitioning of the aqueous residue between ethyl acetate and 1N HCl. The organic phase was washed twice with 1N HCl, once with 5% $NaHCO_3$, dried over sodium sulfate and concentrated to a residue. Flash chromatography (silica gel; hexane/toluene (39/1)) of the residue gave 1.10 g (84%; GC retention time=15.80 minutes) of a water white oil Elemental Analysis: $C_{12}H_{14}C_{12}O_2$ requires C 55.19%, H 5.40%; Found: C 54.95%, H 5.51%.

5-(2,5-Dichlorophenyl)pentanoic acid (Competitor 11)

Methyl 5-(2,5-Dichlorophenyl)pentanoate (1.10 g, 4.2 mmol) was dissolved in 20 ml THF and 7 mL methanol. 1N LiOH (12mL) was added dropwise and the reaction was stirred at room temperature for 2 days. The reaction was worked-up by acidification with 2N HCl and removal of most of the THF and methanol on a rotary evaporator followed by extraction of the aqueous residue with ethyl acetate. The organic phase was washed with water and saturated brine, dried over sodium sulfate and concentrated to a residue. Flash chromatography (silica gel; hexane/toluene (19/1) with 1% acetic acid) of the residue gave 725 mg (70%) of a white solid.

Elemental analysis: $C_{11}H_{12}C_{12}O_2$ requires C 53.54%, H 4.89%; Found: C 53.65%, H 5.00%.

Example 13

Competitor Conjugation

The competitors were conjugated to the carrier protein, bovine serum albumin, using the carbodiimide mediated carboxyl activation procedure described for Hapten I. Competitor loads were determined using the amide hydrolysis and GC quantification procedure described for Hapten I. Examples of competitor conjugates which were prepared are:

| Sample | GC Load | Quantity |
|---|---|---|
| BSA-Competitor 9 Conjugation | 26 | 28 mg |
| BSA-Competitor 9 Control | 3.5 | |
| BSA-Competitor 11 Conjugation | 14 | 17 mg |
| BSA-Competitor 11 Control | 0.8 | |

Example 14

Immunization of Rabbits and Demonstration of Anti-Hapten Response

Groups of six rabbits were immunized with KLH-hapten I conjugate according to the schedule in Table 1. Sera samples (Table 1) were evaluated for anti-hapten titer by ELISA on plates coated with BSA-hapten I conjugate (Method A). Anti-hapten titers of up to 1/67,000 (average of 1/26,000 for the 40–180 day period) demonstrated that a strong anti-hapten antibody response could be produced with these haptens.

TABLE 1

Rabbit Immunization and Bleed Plan

| Immunization | | | Test Bleed |
|---|---|---|---|
| Description | µg. imm. | day | day |
| B pertussis, im | | −3 | −3 |
| 1°-CFA+, mID | 300 µg | 1 | |
| 2°-CFA, sc4 | 200 µg | 14 | |
| 2°-CFA, sc | 100 µg | 21 | |
| | | | 26 |
| b-IFA, sc | 100 µg | 28 | |
| | | | 40 |
| b-IFA, sc | 100 µg | 42 | |
| | | | 54 |
| b-IFA, sc | 100 µg | 56 | |
| | | | 68 |
| | | | 82 |
| b-IFA, sc | 100 µg | 84 | |
| | | | 96 |
| | | | 110 |
| b-IFA, sc | 100 µg | 112 | |
| | | | 124 |
| | | | 138 |
| b-IFA, sc | 100 µg | 140 | |
| | | | 152 |
| | | | 166 |
| b-IFA, sc | 100 µg | 168 | |
| | | | 180 |

Abbreviations
1°: initial challenge solution
2°: secondary challenge solution
b: booster
CFA: complete Freund's adjuvant
CFA+: fortified complete Freund's adjuvant
IFA: incomplete Freund's adjuvant
im: intramuscular
mID: multiple intradermal (30–50 sites)
sc: subcutaneous
sc4: subcutaneous, 4 sites Example 15

Demonstration of the Sera Anti-PCB Response

Sera samples were evaluated in an inhibition ELISA format with a BSA-hapten I coating conjugate (Method B). FIG. 1 (Plot 1) demonstrates the anti-PCB response of the sera with a minimum detection limit ($I_{10}$) of approximately 4 ppm and an $I_{50}$ of approximately 50 ppm for the PCB congener mixture Aroclor® 1248.

Example 16

Demonstration of an Inhibition ELISA Based on a Competitor Conjugate

Inhibition ELISA using a BSA-Competitor 11 coating conjugate (Methods A,B; BSA-Competitor 11 conjugate substituted for hapten conjugate) demonstrated significantly improved PCB sensitivity as is illustrated in FIG. 1 (Plot 3). This assay format gave a minimum detection limit ($I_{10}$) of approximately 0.2 ppm and an $I_{50}$ of approximately 3 ppm. In addition, the assay has been demonstrated to be highly responsive to the major Aroclor® mixtures of PCB congeners (Table 2) and to be nonresponsive to related non-PCB environmental contaminants (Table 3).

TABLE 2

| Competitor 11 Assay Response | | |
|---|---|---|
| Aroclor ® | $I_{10}$(mdl) (ppm) | $I_{50}$(ppm) |
| 1221 | 2.20 | 45.0 |
| 1242 | 0.24 | 3.5 |
| 1248 | 0.18 | 3.5 |
| 1254 | 0.24 | 6.8 |
| 1260 | 0.32 | 7.5 |

TABLE 3

| Selected Analytes - Competitor 11 Assay Response | |
|---|---|
| Analyte | $u^1 10$ (mdl) |
| 1,2-dichlorobenzene | NR/>100 ppm |
| 1,3-dichlorobenzene | NR/>100 ppm |
| 1,4-dichlorobenzene | NR/>100 ppm |
| 1,2,4-trichlorobenzene | NR/>100 ppm |
| 3-chlorophenol | NR/>100 ppm |
| 2,5-dichlorophenol | NR1>100 ppm |
| 2,4-dichlorophenoxyacetic acid | NR/>100 ppm |
| 3-chloroanisole | NR/>100 ppm |

NR — No Assay Response

Example 17

Inhibition ELISA Soil Analysis Demonstration

The Exemplified Competitor 11 based inhibition ELISA was used with a simple solvent extraction step (Method C), which was not recovery optimized, to demonstrate the application of the assay to the screening of soil samples for PCB contamination (Table 4). The assay has been demonstrated to be relatively free of matrix extract interferences and to readily provide a measure of PCB content in the sample of less than 5 ppm.

TABLE 4

| ELISA Analysis of Soil Extracts Clay Soil 1× Extracts | | |
|---|---|---|
| Sample | $B/B_o$ | Aroclor 1248 |
| 0 ppm | 1.02 | — |
| 0.005 ppm | 1.08 | ND[1] |
| 0.05 ppm | 1.08 | ND |
| 0.5 ppm | 1.01 | ND |
| | mdl = 0.90 $B/B_o$ | |
| 5 ppm | 0.856 | 3.69 sd 0.13 ppm |
| 50 ppm | 0.433 | 38.2 sd 3.0 ppm |

(1) [1]ND — Not Detected, Below mdl (minimum detection level)

Example 18

Results using Exemplified Competitor 11 with Hapten II were similar to those obtained for Hapten I.

Example 19

METHOD D: Enzyme Immunoassay (EIA)

Serum stored at −20° C. was diluted 1,000–40,000 fold with PBS which contained 0.1% Tween-20. This solution was dispensed (500 μl) into goat anti-rabbit second antibody coated tubes (GAR Tubes commercially available from Millipore Corp., Bedford, Mass.) and incubated at room temperature overnight. The antisera solution was decanted from the tubes and the tubes were washed 3 times with distilled water. Non-specific sites in the tubes were blocked with 600 μl of a BSA blocking buffer (EIA Blocking Buffer commercially available from Millipore Corp., Bedford, Mass.) and incubated for 2 hours at room temperature or overnight at 4° C. The blocking buffer was decanted and the tubes allowed to dry under ambient room conditions for 2 hours or overnight. The assay was performed by adding 500 μl of assay diluent (1% methanol (v/v) and 0.005% -Tween-20 (w/v) in distilled water) to the required number of tubes followed by 10 μl of a methanol solution which contained 0–50 ppm of Aroclor 1248. After a 5 minute incubation at room temperature, the solution was decanted and the tubes rinsed 3–4 times with tap water. The horseradish peroxidase-(HRP) competitor conjugate or Hapten I conjugates were diluted 100–100,000 fold from 2–5 mg/ml stock solutions in PBS with conjugate diluent (Enzyme Conjugate Diluent commercially available from Millipore Corp., Bedford, Mass.). Enzyme-competitor conjugate was added in 200 μl and the tubes were incubated at room temperature for 5 minutes. The conjugate solution was decanted and the tubes rinsed 3–4 times with tap water. Enzyme substrate solution (500 μl , KPL No. 50–76–04 commercially available from KPL Laboratories, Gaithersburg, Md.) was added and the tubes were incubated at room temperature for 3–15 minutes. The enzyme reaction was stopped with the addition of 500 μl of 1N HCl. The OD of the solution was determined at 450 nm and the $I_{50}$ values were determined using a correlation of Log (Aroclor 1248 Concentration in the assay solution in parts per billion=ppb) versus B/Bo ratio where B=Sample Absorbance and Bo=Absorbance of the Blank Sample.

Example 20

Synthesis of Exemplified Competitors 9 and 11–17

Exemplified Competitors 9 and 11–17 are readily available from commercial sources or via known syntheses.

| Competitor | Source |
|---|---|
| 9 | Commercial Product, Trans-World Organics, Trans-World Chemicals, Inc., Chevy Chase, Maryland |
| 11 | Described in Example 12 |
| 12 | Known Synthesis, reference A. Rosowsky et al., J. Hetero. Chem., 8, 789–793 (1971) |
| 13 | Known Synthesis, K. Rashid, J. Environ. Sci. Health, Part B, B22, 721–729 (1987) |
| 14 | Commercial Product, Aldrich Chemical Co. |
| 15 | Commercial Product, Aldrich Chemical Co. |
| 16 | Known Synthesis, V. Tandon et al., Indian J. Chem., Sect. B., 15B 264–266 (1977) |
| 17 | Known Synthesis, S. Kukalenko, Zh. Org. Khim, 6, 680–684 (1970) |

Example 21

Preparation of Enzyme Conjugates

The competitors and Hapten I were conjugated to the enzyme, amino modified Horseradish Peroxidase (HRP) (horseradish peroxidase commercially available from Sigma Chemical Co. (No. P-6782), St. Louis, Mo.; amino modified per ref R. Hsiao and H. Royer, *Archives Biochem. Biophys-* ics, 198, 379–385 (1979) to give 6–24 free amines), using the carbodiimide mediated carboxyl activation procedure described for Hapten I in Example 5.

Example 22

Demonstration of the EIA Based on Competitor Conjugates

Figure 4:
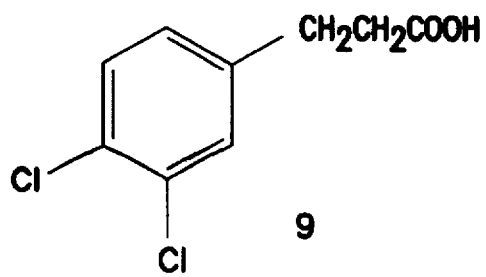
FIG. 4 presents structures of exemplified competitors. Numbering of the competitors has been continued from the exemplified competitors on p. 17 of the application.
Figure 4:
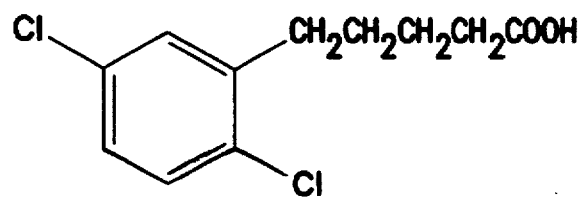
Figure 4:
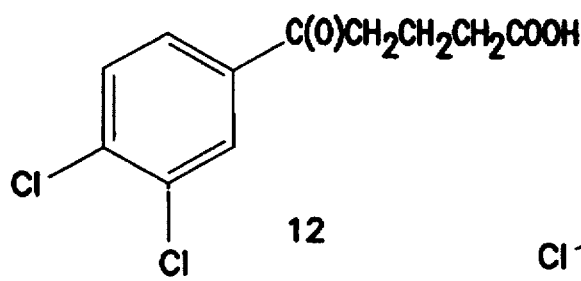
Figure 4:
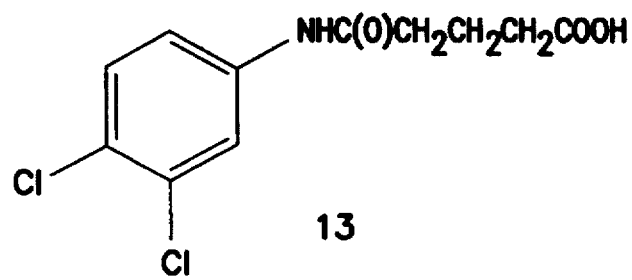
Figure 4:
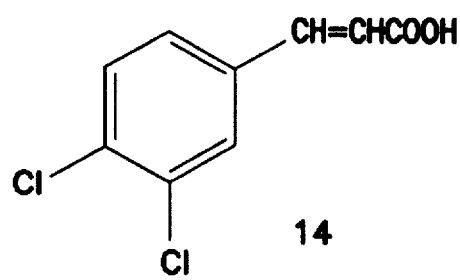
Figure 4:
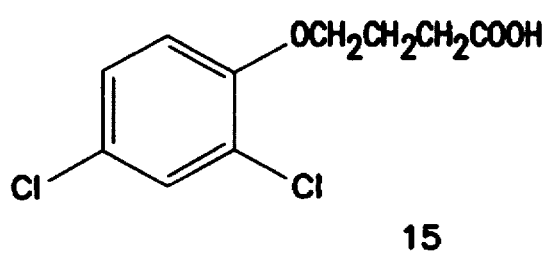
Figure 4:
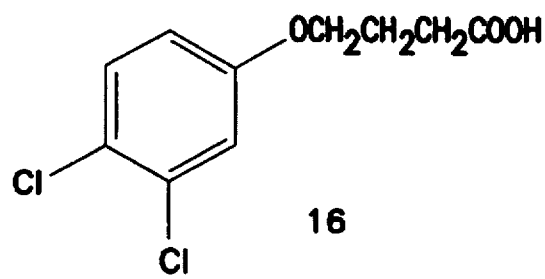
Figure 4:
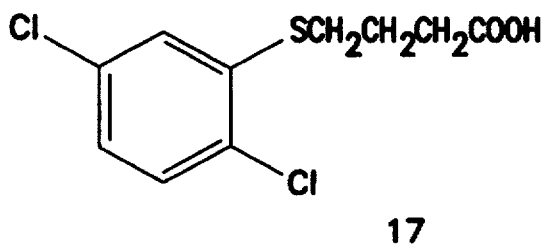

EIA analysis of Aroclor 1248 (Method D) was performed using horseradish peroxidase (HRP) Conjugates of the competitors illustrated in FIG. 4. Comparison of the Aroclor 1248 sensitivity of the exemplified competitors versus Hapten I assay (Table 5) demonstrates the general utility of the competitors in the development of assays with improved analyte sensitivity.

TABLE 5

Comparison of PCB EIA Sensitivity Using Selected Exemplified Competitors.

| Exemplified Competitor | Assay Response ($I_{50}$) (1) | Relative Response (2) |
| --- | --- | --- |
| 9 | 47 ppb | 12 fold |
| 11 | 18 ppb | 32 fold |
| 12 | 23 ppb | 24 fold |
| 13 | 2000 ppb | <1 fold |
| 14 | 64 ppb | 9 fold |
| 15 | 49 ppb | 12 fold |
| 16 | 31 ppb | 18 fold |
| 17 | 33 ppb | 18 fold |
| Homologous (Hapten I) | 570 ppb | -1- |

(1) Defined as the assay solution concentration of Aroclor 1248 which produces a 50% reduction in the assay control signal.
(2) Defined as the relative improvement in $I_{50}$ sensitivity compared to the homologous (Hapten I) based assay; e.g. an $I_{50}$ of 10 ppb is a 10 fold improvement in sensitivity relative to an $I_{50}$ of 100 ppb.

All patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

We claim:

1. A method for determining qualitatively or quantitatively the presence of polychlorinated biphenyl in a test sample comprising the steps of:

A) providing a known quantity of antibodies to polychlorinated biphenyl;

B) providing a competitor that will bind to said antibodies in competition with polychlorinated biphenyl; wherein said competitor has one of the following structures:

FORMULA I

[structure: benzene ring with A—B—C substituent and $Cl_n$]

FORMULA II

[structure: biphenyl with $Cl_p$, A—B—C, Y, Y', $Cl_q$]

wherein
(a) A is selected from the group consisting of —S—, —CH$_2$—, and —C(O)—NH—;
(b) B is a single bond or an organic or inorganic linking group capable of forming covalent bonds with A and C simultaneously;
(c) C is selected from the group consisting of —CO$_2$H, —NH$_2$, —CHO, and —OH;
(d) Y and Y' are selected from the group consisting of —H and —Cl;
(e) n=0–5;
(f) p=0–3; and
(g) q=0–4;

C) incubating said antibodies and said competitor in the presence of a test sample; and D) detecting the presence of polychlorinated biphenyl in the test sample.

2. The method of claim 1 wherein the competitor has the general structure of Formula I.

3. The method of claim 2 wherein B is a C$_1$–C$_{10}$ alkyl, or C$_1$–C$_{10}$ alkyl including —S—, —NH—, or 1–4 nonperoxide —O—.

4. The method of claim 1 wherein both y and Y' are —Cl.

5. The method of claim 1 wherein said competitor is bound to a solid support.

6. The method of claim 1 wherein the step of detecting the presence of polychlorinated biphenyl comprises the use of an enzymatic label.

7. The method of claim 6 wherein the step of detecting the presence of polychlorinated biphenyl is the use of an ELISA determination.

8. The method of claim 1 wherein said antibodies are prepared by inoculating a host animal with a hapten-protein complex, wherein the hapten has the following structure and collecting the serum from the host animal:

FORMULA III

[structure: biphenyl with $Cl_p$, L—M—N, Y, Y', $Cl_q$]

wherein
(a) L is selected from the group consisting of —NH—, —S—, —O—, —CH$_2$—, —NH—C(O)—, —C(O)—NH—, —NH—C(O)—NH—, —NH—C(S)—NH—, —N(CH$_3$)—, —N(CH$_3$)$_2$—, and —OC(S)NH—;
(b) M is a single bond or an organic or inorganic linking group capable of forming covalent bonds with L and N simultaneously;

(c) N is selected from the group consisting of —CO₂H, —NH₂, —CHO, and —OH;

(d) Y and Y' are selected from the group consisting of —H and —Cl, with the proviso that at least one of Y and Y' is —Cl;

(e) p=0–3; and (f) q=0–4.

9. The method of claim 8 wherein the hapten is covalently bound to a protein.

10. The method of claim 1 wherein A is selected from the group consisting of —S— and —CH₂—.

11. The method of claim 10 wherein A is —CH₂—.

12. The method of claim 1 wherein n=1–3.

13. The method of claim 1 wherein the competitor is bound to a protein.

14. A method for determining qualitatively or quantitatively the presence of polychlorinated biphenyl in a test sample comprising the steps of:

A) providing a known quantity of antibodies to polychlorinated biphenyl;

B) providing a competitor that will bind to said antibodies in competition with polychlorinated biphenyl; wherein said competitor has the following structure:

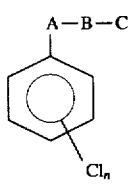

FORMULA I wherein (a) A is selected from the group consisting of —NH—, —S—, —O—, —CH₂—, —NH—C(O)—, —C(O)—NH—, —NH—C(O)—NH—, —NH—C(S)—NH—, —N(CH₃)—, and —N(CH₃)₂—, and —O—C(S)—NH—;

(b) B is a single bond or an organic or inorganic linking group capable of forming covalent bonds with A and C simultaneously;

(c) C is selected from the group consisting of —CO₂H, —NH₂, —CHO, and —OH; and (d) n=0–5;

C) incubating said antibodies and said competitor in the presence of a test sample; and D) detecting the presence of polychlorinated biphenyl in the test sample.

15. The method of claim 14 wherein A is selected from the group consisting of —NH—, —S—, —O—, and —CH₂—.

16. The method of claim 14 wherein B is a C₁–C₁₀ alkyl, or C₁–C₁₀ alkyl containing —S—, —NH—, or 1–4 nonperoxide —O—.

17. The method of claim 14 wherein the step of detecting the presence of polychlorinated biphenyl comprises the use of an enzymatic label.

18. The method of claim 14 wherein n=1–3.

19. The method of claim 14 wherein said antibodies are prepared by inoculating a host animal with a hapten-protein complex, wherein the hapten has the following structure and collecting the serum from the host animal:

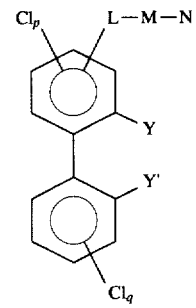

FORMULA III wherein (a) L is selected from the group consisting of —NH—, —S—, —O—, —CH₂—, —NH—C(O)—, —C(O)—NH—, —NH—C(O)—NH—, —NH—C(S)—NH—, —N(CH₃)—, —N(CH₃)₂—, and —OC(S)NH—;

(b) M is a single bond or an organic or inorganic linking group capable of forming covalent bonds with L and N simultaneously;

(c) N is selected from the group consisting of —CO₂H, —NH₂, —CHO, and —OH;

(d) Y and Y' are selected from the group consisting of —H and —Cl, with the proviso that at least one of Y and Y' is —Cl;

(e) p=0–3; and (f) q=0–4.

20. The method of claim 14 wherein the competitor is

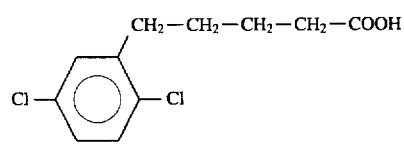

21. The method of claim 14 wherein the competitor is bound to a protein.

22. The method of claim 14 wherein the competitor is bound to a solid support.

* * * * *

UNITED STATES PATENT AND TRADEMARK OFFICE
CERTIFICATE OF CORRECTION

PATENT NO. : 5,538,852           Page 1 of 2
DATED      : July 23, 1996
INVENTOR(S): Carlson, et al It is certified that error appears in the above-indentified patent and that said Letters Patent is hereby corrected as shown below:

Column 5, line 32, delete "-N N$_2$" and insert therefor --NH$_2$--

Column 14, line 27, delete "C$_3$H$_8$OCl$_4$" and insert therefor --C$_{13}$H$_8$OCl$_4$--.

Column 14, line 34, delete "methoxybiphenylderivatives" and insert therefor --methoxylbiphenyl derivatives--.

Column 15, line 48, delete "419. 9872" and insert therefor --419.9872--.

Column 15, line 63, delete "UV/V" and insert therefor --UV/Vis--.

UNITED STATES PATENT AND TRADEMARK OFFICE
CERTIFICATE OF CORRECTION

PATENT NO. : 5,538,852

DATED : July 23, 1996

INVENTOR(S) : Carlson et al.

It is certified that error appears in the above-indentified patent and that said Letters Patent is hereby corrected as shown below:

Column 23, line 22, delete "NRI>100ppm" and insert therefor --NR/>100ppm--.

Column 26, line 35, delete "y" and insert therefor --Y--.

Signed and Sealed this

Seventh Day of January, 1997

Attest:

BRUCE LEHMAN

*Attesting Officer*      *Commissioner of Patents and Trademarks*